United States Patent [19]

Ohsawa et al.

[11] Patent Number: 5,847,218

[45] Date of Patent: Dec. 8, 1998

[54] SULFONIUM SALTS AND CHEMICALLY AMPLIFIED POSITIVE RESIST COMPOSITIONS

[75] Inventors: Youichi Ohsawa; Satoshi Watanabe; Junji Shimada; Katsuya Takemura; Shigehiro Nagura; Toshinobu Ishihara, all of Niigata-ken, Japan

[73] Assignee: Shin-Etsu Chemical Co., Ltd., Tokyo, Japan

[21] Appl. No.: 811,530

[22] Filed: Mar. 4, 1997

[30] Foreign Application Priority Data

Mar. 5, 1996 [JP] Japan ...................................... 8-075342

[51] Int. Cl.[6] .................................................. C07C 211/44
[52] U.S. Cl. ........................ 564/430; 546/266; 430/270.1
[58] Field of Search ............................ 564/430; 546/266; 430/270.1

[56] References Cited

U.S. PATENT DOCUMENTS

| | | | |
|---|---|---|---|
| 3,929,886 | 12/1975 | Isard et al. | 260/567.6 R |
| 4,883,740 | 11/1989 | Schwalm et al. | 430/270 |
| 5,006,449 | 4/1991 | Toya et al. | 430/508 |
| 5,084,371 | 1/1992 | Schwalm et al. | 430/270 |
| 5,191,124 | 3/1993 | Schwalm et al. | 568/18 |
| 5,569,784 | 10/1996 | Watanabe et al. | 564/430 |

FOREIGN PATENT DOCUMENTS

| | | |
|---|---|---|
| 64-12153 | 1/1989 | Japan . |
| 64-26550 | 1/1989 | Japan . |
| 64-35433 | 2/1989 | Japan . |
| 5-232706 | 9/1993 | Japan . |
| 5-249683 | 9/1993 | Japan . |
| 7-252214 | 10/1995 | Japan . |

*Primary Examiner*—Brian M. Burn
*Attorney, Agent, or Firm*—Millen, White, Zelano & Branigan, P.C.

[57] ABSTRACT

The invention provides a novel sulfonium salt having a substituted or unsubstituted arylsulfonate anion. The novel sulfonium salt minimizes the influence of deactivation by basic compounds not only at a resist surface, but also at a resist-substrate interface, assists a resist to be configured to a definite pattern profile. When the sulfonium salt has an acid labile group, it is effective for increasing the dissolution contrast between exposed and unexposed areas. The sulfonium salt is useful in a chemically amplified positive resist composition which lends itself to fine patterning and features high resolution.

19 Claims, No Drawings

SULFONIUM SALTS AND CHEMICALLY AMPLIFIED POSITIVE RESIST COMPOSITIONS

BACKGROUND OF THE INVENTION

1. Field of the Invention

This invention relates to a novel sulfonium salt and a chemically amplified positive resist composition containing the same and suitable for use in fine patterning.

2. Prior Art

As the LSI technology tends toward higher integration and higher speed, further refinement of pattern rules is required. Deep-ultraviolet lithography is regarded promising as the next generation of fine patterning technology. The deep-UV lithography is capable of working on the order of 0.3 to 0.4 μm. If a less light absorbing resist is used, it is possible to form a pattern having a side wall nearly perpendicular to the substrate. Great attention is now paid to the technique of utilizing a high illuminance KrF excimer laser as a deep-UV light source. In order to employ this technique on a mass production scale, a resist material having low light absorption and high sensitivity is desired.

From this point of view, a number of chemically amplified positive working resist materials using acid catalysts were recently developed as disclosed in U.S. Pat. Nos. 4,491,628, 5,310,619 and 5,362,607. These materials have high sensitivity, resolution and dry etching resistance and are promising as resist materials especially suited for deep-UV lithography.

It is known that the function of chemically amplified positive resist materials is largely affected by photoacid generators used therein. Typical photoacid generators are onium salts as shown below.

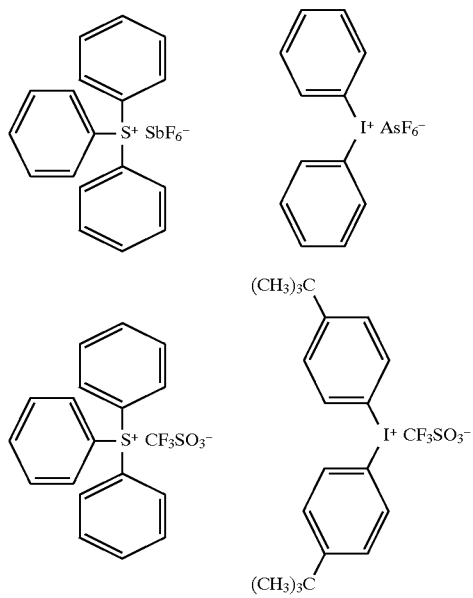

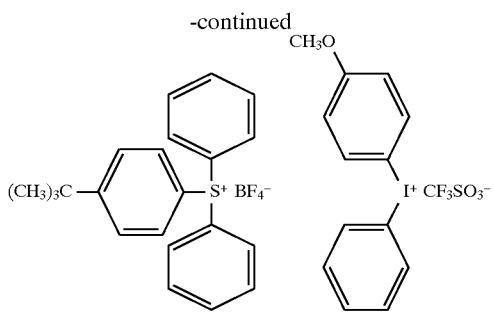

The onium salts themselves are lipophilic. When blended as a resist component, they act to reduce the solubility of the resist material in alkaline aqueous solution and to prevent the resist film from thinning upon development.

However, in exposed areas of positive resist material, photoacid generators absorb actinic radiation to decompose into products which are also lipophilic. The decomposed products reduce the rate of dissolution of the exposed areas in alkaline aqueous solution, failing to provide a high ratio of the alkali dissolution rate of exposed areas to that of unexposed areas (which ratio is known as dissolution contrast).

This problem can be solved by incorporating a tert-butoxycarbonyl group or acid labile group into p-hydroxyphenylsulfonium salts as disclosed in JP-A 26550/1989, 35433/1989, and 12153/1990. Upon exposure to actinic radiation, the salts decompose to generate acids, which help form alkali soluble phenol derivatives, providing an enhanced dissolution contrast. These tert-butoxycarbonyl-oxyphenylsulfonium salts, however, lack thermal stability and fail to satisfy the requirement of high resolution. Additionally, they generate strong acids such as metal halide anions and trifluoromethanesulfonic acid. Since the generated acid has high acidity, an acid labile group can be effectively decomposed with a small amount of acid. However, since the amount of acid generated is very small, line patterns would have a T-top profile, that is, patterns become thick at the top if the leave-to-stand or delay time from exposure to post-exposure baking (PEB) is extended. Patterns tend to be readily affected by contamination with air-borne basic compounds. This phenomenon is known as post exposure delay (PED).

It is known from JP-A 232706/1993 and 249683/1993 to add a basic compound in a resist material for suppressing the influence of air-borne basic compounds. According to our follow-up test, the basic compound used therein is little taken into the resist film due to volatilization, less compatible with resist components, and unevenly dispersible in a resist film. Thus the basic compound cannot achieve its advantages in a reproducible manner and causes a drop of resolving power.

In order to reduce the influence of air-borne basic compounds, JP-A 252214/1995 proposes use of a sulfonium salt having a trifluoromethanesulfonate anion and a nitrogenous aromatic group. We confirmed that when such a nitrogenous sulfonium salt was used as one component of a chemically amplified positive working resist composition, it was well compatible and dispersible, reduced the influence of air-borne basic compounds, and eliminated a footing problem of a pattern profile on a silicon oxide substrate. However, a footing problem occurred in a pattern profile when a nitride film substrate was used. A substantial difference in pattern profile occurs between different substrates. That is, stability depends on the identity of substrate.

It is believed that this problem arises for the following reason. Like air-borne basic compounds, at an area of contact between a resist film and a substrate, basic compounds on the substrate surface react with the resist film to deactivate the acid to form a difficultly soluble layer on the substrate surface, resulting in a footing profile. The footing profile is highly substrate dependent. Where the substrate is a nitride film such as silicon nitride and titanium nitride, a N—H bond in the nitride film reacts with acid. Where the substrate is titanium nitride, titanium nitride itself reacts with acid. In either case, the acid available at the chemically amplified resist-nitride film substrate interface is deactivated. See J. Photopolym. Sci. and Tech., 1995, 8 (4), 571–598.

It is also reported in Proc. SPIE, 2195, 74–83 (1994) that strong acids such as trifluoromethanesulfonic acid resulting from photolysis reaction give rise to undesired side reaction during the PEB step involving decomposition of a tert-butoxycarbonyloxyphenyl group or acid labile group, forming a by-product having a hydroxyphenyl group tert-butylated at the opposition which causes a drop of alkali solubility.

When a photoacid generator which generates an unsubstituted alkylsulfonic acid which is weaker than conventional trifluoromethanesulfonic acid is used, the pattern configuration changes only a little even when the leave-to-stand time from exposure to post-exposure baking (PEB) is extended. There can still occur problems that less efficient decomposition of an acid labile group requires more acid, a drop of sensitivity requires an extended exposure time, device manufacture becomes difficult, and the weak acid would cause the acid labile group to be decomposed to an insufficient extent to form a pattern profile.

It is desired to overcome the above-mentioned problems associated with chemically amplified positive resist materials.

SUMMARY OF THE INVENTION

Therefore, an object of the present invention is to provide a novel sulfonium salt suitable for use in a chemically amplified positive resist composition having sufficiently high resolution to comply with a fine patterning technique. Another object of the present invention is to provide a chemically amplified positive resist composition containing the novel sulfonium salt.

We have found that by reacting a substituted diaryl sulfoxide of the general formula (2) with a trialkylsilylarylsulfonate of the general formula (3) and further with a Grignard reagent of the general formula (4) (obtained by reacting a substituted or unsubstituted phenyl chloride or bromide with magnesium) according to the reaction scheme shown below, there can be produced a novel sulfonium salt having a substituted or unsubstituted arylsulfonate anion of the general formula (1).

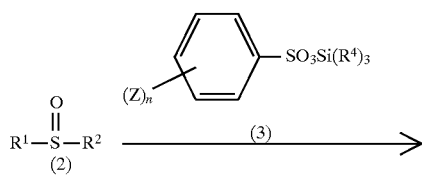

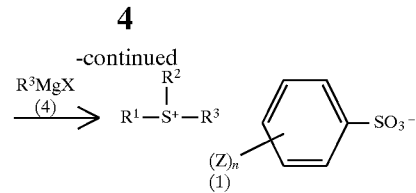

In the formulae, each of $R^1$, $R^2$, and $R^3$ is a substituted or unsubstituted aromatic group, at least one of $R^1$, $R^2$, and $R^3$ is a substituted aromatic group having an acid labile group and at least one of the remaining two is a nitrogenous aromatic group or all of $R^1$, $R^2$, and $R^3$ are nitrogenous aromatic groups; $R^4$ is an alkyl group; Z is a hydrogen atom, alkyl group or alkoxy group; x is chlorine or bromine; and letter n is an integer of 1 to 5.

Using the sulfonium salt of formula (1) as a resist component, there is obtained a chemically amplified positive resist composition which has sufficiently high resolution to comply with a fine patterning technique and is especially effective with deep-UV lithography.

The following advantages are obtainable where the sulfonium salt of formula (1) is used as one component of a chemically amplified positive resist composition. The nitrogenous substituent and (substituted or unsubstituted) arylsulfonate anion of the sulfonium salt of formula (1) are effective for minimizing the influence of deactivation of generated acid at the resist surface by basic compounds and suppressing the development of a difficultly soluble surface layer. Even when a nitride film substrate, that is, a substrate having a basic compound on the surface is used, the sulfonium salt of formula (1) is effective for suppressing degradation of a pattern profile and minimizing a footing profile. Since the nitrogenous substituent has been incorporated in the sulfonium salt which is a photoacid generator, it is well compatible with resist components and evenly dispersible in a resist film and achieves its advantages in a reproducible manner owing to its low volatility.

Although the sulfonium salt itself has low alkali solubility when it has an acid labile group, it is decomposed to generate an acid upon exposure to actinic radiation. This acid, combined with a water content in the resist material and the post-exposure bake (PEB), serves to effectively decompose the acid labile group to form a phenol position having high alkali solubility or a carboxylic acid position having high alkali solubility where the acid labile group is a tertiary carboxylate group such as tert-butoxycarbonylmethyloxy group, providing a higher dissolution contrast.

Moreover, the acid generated upon exposure to actinic radiation is neither a strong acid like conventional trifluoromethanesulfonic acid nor a too weak alkylsulfonic acid, but a substituted or unsubstituted arylsulfonic acid having an intermediate acidity. This not only minimizes the side reaction associated with strong acids and the influence of deactivation of the once generated acid by air-borne basic compounds on the resist film surface and at the resist film-wafer substrate interface, but also eliminates insufficient decomposition of an acid labile group as found with the use of weak acids like alkylsulfonic acids. This ensures high sensitivity.

Therefore, the sulfonium salt of formula (1) performs well as a photoacid generator for a chemically amplified positive resist composition. The nitrogenous substituent and (substituted or unsubstituted) arylsulfonate anion of the sulfonium salt of formula (1) are effective for minimizing the influence of deactivation of generated acid at the resist surface and resist film-substrate interface by basic compounds. In the embodiment wherein the sulfonium salt of formula (1) has an acid labile group, the resist composition will form a resist pattern having a high dissolution contrast, high resolution, a wide range of focal depth, and environmental stability, owing to the function of acid labile group.

Accordingly, the present invention in a first aspect provides a sulfonium salt of formula (1) having a substituted or unsubstituted arylsulfonate anion.

In a second aspect, the present invention provides a chemically amplified positive resist composition comprising a sulfonium salt of formula (1). Also contemplated herein are a chemically amplified positive resist composition comprising (A) an organic solvent, (B) an alkali soluble resin, (C) a dissolution inhibitor having an acid labile group, (D) a sulfonium salt of formula (1), and (E) a photoacid generator, and a chemically amplified positive resist composition comprising (A) an organic solvent, (B) an alkali soluble resin, (D) a sulfonium salt of formula (1), and (E) a photoacid generator.

DETAILED DESCRIPTION OF THE INVENTION

In the first aspect, the present invention provides a novel sulfonium salt having a substituted or unsubstituted arylsulfonate anion. The sulfonium salt is represented by the following general formula (1):

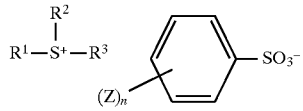

wherein each of $R^1$, $R^2$, and $R^3$ is a substituted or unsubstituted aromatic group, at least one of $R^1$, $R^2$, and $R^3$ is a substituted aromatic group having an acid labile group and at least one of the remaining two is a nitrogenous aromatic group or all of $R^1$, $R^2$, and $R_3$ are nitrogenous aromatic groups; Z is a hydrogen atom, alkyl group or alkoxy group; and letter n is an integer of 1 to 5.

In formula (1), each of $R^1$, $R^2$, and $R^3$, which may be identical or different, is a substituted or unsubstituted aromatic group. Included are phenyl, alkylphenyl groups, alkoxyphenyl groups, aromatic groups having an acid labile group other than alkoxy, and nitrogenous aromatic groups. Exemplary alkylphenyl groups are those wherein the alkyl group has 1 to 8 carbon atoms, including methylphenyl, ethylphenyl, propylphenyl, isopropylphenyl, n-butylphenyl, sec-butylphenyl, tert-butylphenyl, hexylphenyl, and cyclohexylphenyl groups, with the methylphenyl, ethylphenyl, n-propylphenyl, isopropylphenyl, and tert-butylphenyl groups being preferred. Exemplary alkoxyphenyl groups are those wherein the alkoxy group has 1 to 8 carbon atoms, including methoxyphenyl, ethoxyphenyl, propoxyphenyl, isopropoxyphenyl, n-butoxyphenyl, sec-butoxyphenyl, hexyloxyphenyl, and cyclohexyloxyphenyl groups, with the methoxyphenyl, ethoxyphenyl, and isopropoxyphenyl groups being preferred.

In conjunction with the aromatic group having an acid labile group, examples of the acid labile group include tertiary alkoxy groups such as tert-butoxy; carbonate groups such as tert-butoxycarbonyloxy; tertiary carboxylate groups such as tert-butoxycarbonylmethyloxy; trialkylsilyloxy groups such as trimethylsilyloxy, triethylsilyloxy, and tert-butyl-dimethylsilyloxy; and acetal and ketal groups such as tetrahydrofuranyloxy, tetrahydropyranyloxy, 2-methoxytetra-hydropyranyloxy, methoxymethyloxy, 1-ethoxyethoxy, 1-propoxyethoxy, 1-n-butoxyethoxy, 1-iso-butoxyethoxy, 1-sec-butoxyethoxy, 1-tert-butoxyethoxy, 1-amyloxyethoxy, 1-ethoxy-1-methylethoxy, 1-propoxy-1-methylethoxy, 1-n-butoxy-1-methylethoxy, 1-isobutoxy-1-methylethoxy, 1-sec-butoxy-1-methylethoxy, 1-tert-butoxy-1-methylethoxy, and 1-amyloxy-1-methylethoxy groups. Preferred examples of the aromatic group having an acid labile group are tert-butoxyphenyl, tert-butoxycarbonylmethyloxyphenyl, (1-ethoxyethoxy)phenyl, tetrahydropyranyloxyphenyl, and tetrahydrofuranyloxyphenyl groups.

Examples of the nitrogenous aromatic group include dialkylaminophenyl groups wherein the alkyl group has 1 to 8 carbon atoms, picolyloxyphenyl groups, and pyridinyl groups. Preferred are dialkylaminophenyl groups wherein the alkyl group has 1 to 4 carbon atoms.

In formula (1), at least one of $R^1$, $R^2$, and $R^3$ is a substituted aromatic group having an acid labile group and at least one of the remaining two is a nitrogenous aromatic group. Alternatively, all of $R^1$, $R^2$, and $R^3$ are nitrogenous aromatic groups.

These substituted aromatic groups may have a substituent at any of o-, m- and p-positions. Among these aromatic groups, p-substituted ones have high molecular crystallinity or symmetry and m-substituted ones have high transmittance at 248 nm. In the case of o-substituted aromatic groups wherein the substituent has greater steric hindrance, few of desired sulfonium salts are obtainable.

Next, the substituent Z of the substituted or unsubstituted arylsulfonate anion is a hydrogen atom, alkyl group or alkoxy group. The alkyl groups are preferably normal and branched alkyl groups having 1 to 12 carbon atoms, for example, methyl, ethyl, sec-propyl, n-butyl, tert-butyl, n-octyl, and n-dodecyl groups. The alkoxy groups are preferably those having 1 to 8 carbon atoms, for example, methoxy, ethoxy, n-propoxy, isopropoxy, n-butoxy, sec-butoxy, hexyloxy, and cyclohexyloxy groups, with the methoxy, ethoxy, and isopropoxy groups being preferred. The position and number of such substituents are not critical.

It is essential that the substituent Z of the substituted or unsubstituted arylsulfonate anion excludes electron attractive groups such as a fluorine atom and nitro group.

Examples of the substituted or unsubstituted arylsulfonate anion include a benzenesulfonate anion, p-toluenesulfonate anion, o-toluenesulfonate anion, p-ethylbenzenesulfonate anion, p-tert-butylsulfonate anion, p-n-octylbenzenesulfonate anion, 2,4-dimethylbenzenesulfonate anion, and 2,5-dimethylbenzenesulfonate anion.

Where a novel sulfonium salt having a substituted or unsubstituted arylsulfonate anion, which becomes a weaker acid than trifluoromethane sulfonic acid, and a nitrogenous aromatic group according to the invention is used as one component of a resist composition, the anion and the nitrogenous aromatic group are effective for minimizing the influence of deactivation of the acid at the resist film surface by air-borne basic compounds, thereby suppressing formation of a difficultly soluble surface layer, which causes a T-top profile, and improving PED stability. That is, the PED problem is fully overcome. Additionally, even when a substrate in which once generated acid tends to be deactivated at a substrate interface, for example, a nitride film is used, profile degradation such as footing is eliminated. A drop of sensitivity and insufficient decomposition of an acid labile group which otherwise occur when weak acids such as alkylsulfonic acids are used are also eliminated. Higher sensitivity is thus ensured.

Illustrative, non-limiting examples of the sulfonium salt of formula (1) are given below.

Examples of sulfonium salts having a 4-dimethylaminophenyl group as the nitrogenous aromatic group include:

tris(4-dimethylaminophenyl)sulfonium p-toluenesulfonate,
bis(4-tert-butoxyphenyl)(4-dimethylaminophenyl) sulfonium p-toluenesulfonate,
(4-tert-butoxyphenyl)bis(4-dimethylaminophenyl) sulfonium p-toluenesulfonate,
bis(4-tert-butoxycarbonylmethyloxyphenyl)(4-dimethylamino-phenyl)sulfonium p-toluenesulfonate,
(4-tert-butoxycarbonylmethyloxyphenyl)bis(4-dimethylamino-phenyl)sulfonium p-toluenesulfonate,
bis(4-(1-ethoxyethyloxy)phenyl)(4-dimethylaminophenyl)-sulfonium p-toluenesulfonate,
(4-(1-ethoxyethyloxy)phenyl)bis(4-dimethylaminophenyl)-sulfonium p-toluenesulfonate,
bis(4-tetrahydropyranyloxyphenyl)(4-dimethylaminophenyl)-sulfonium p-toluenesulfonate,
(4-tetrahydrofuranyloxyphenyl)bis(4-dimethylaminophenyl)-sulfonium p-toluenesulfonate,
tris(4-dimethylaminophenyl)sulfonium p-ethylbenzenesulfonate,
bis(4-tert-butoxyphenyl)(4-dimethylaminophenyl) sulfonium p-ethylbenzenesulfonate,
(4-tert-butoxyphenyl)bis(4-dimethylaminophenyl) sulfonium p-ethylbenzenesulfonate,
tris(4-dimethylaminophenyl)sulfonium 2,4-dimethylbenzene-sulfonate,
bis(4-tert-butoxyphenyl)(4-dimethylaminophenyl) sulfonium 2,4-dimethylbenzenesulfonate,
(4-tert-butoxyphenyl)bis(4-dimethylaminophenyl) sulfonium 2,4-dimethylbenzenesulfonate,
(4-tert-butoxyphenyl)bis(4-dimethylaminophenyl) sulfonium p-tert-butylbenzenesulfonate,
bis(4-tert-butoxycarbonylmethyloxyphenyl)(4-dimethylamino-phenyl)sulfonium 2,5-dimethylbenzenesulfonate,
(4-tert-butoxycarbonylmethyloxyphenyl)bis(4-dimethylamino-phenyl)sulfonium n-octylbenzenesulfonate,
tris(4-dimethylaminophenyl)sulfonium p-tert-butylbenzene-sulfonate,
bis(4-tert-butoxyphenyl)(4-dimethylaminophenyl) sulfonium p-tert-butylbenzenesulfonate,
(4-tert-butoxyphenyl)bis(4-dimethylaminophenyl) sulfonium benzenesulfonate,
bis(4-tert-butoxycarbonylmethyloxyphenyl)(4-dimethylamino-phenyl)sulfonium benzenesulfonate,
(4-tert-butoxycarbonylmethyloxyphenyl)bis(4-dimethylamino-phenyl)sulfonium benzenesulfonate, etc.

Examples of sulfonium salts having a 3-dimethylaminophenyl group as the nitrogenous aromatic group include:
tris(3-dimethylaminophenyl)sulfonium p-toluenesulfonate,
bis(4-tert-butoxyphenyl)(3-dimethylaminophenyl) sulfonium p-toluenesulfonate,
(4-tert-butoxyphenyl)bis(3-dimethylaminophenyl) sulfonium p-toluenesulfonate,
bis(4-tert-butoxycarbonylmethyloxyphenyl)(3-dimethylamino-phenyl)sulfonium p-toluenesulfonate,
(4-tert-butoxycarbonylmethyloxyphenyl)bis(3-dimethylamino-phenyl)sulfonium p-toluenesulfonate,
bis(4-(1-ethoxyethyloxy)phenyl)(3-dimethylaminophenyl)-sulfonium p-toluenesulfonate,
(4-(1-ethoxyethyloxy)phenyl)bis(3-dimethylaminophenyl)-sulfonium p-toluenesulfonate,
bis(4-tetrahydropyranyloxyphenyl)(3-dimethylaminophenyl)-sulfonium p-toluenesulfonate,
(4-tetrahydrofuranyloxyphenyl)bis(3-dimethylaminophenyl)sulfonium p-toluenesulfonate,
tris(3-dimethylaminophenyl)sulfonium p-ethylbenzenesulfonate,
bis(4-tert-butoxyphenyl)(3-dimethylaminophenyl) sulfonium 2,4-dimethylbenzenesulfonate,
(4-tert-butoxycarbonylmethyloxyphenyl)bis(3-dimethylamino-phenyl)sulfonium n-octylbenzenesulfonate,
bis(4-tert-butoxyphenyl)(3-dimethylaminophenyl) sulfonium benzenesulfonate,
(4-tert-butoxyphenyl)bis(3-dimethylaminophenyl) sulfonium p-tert-butylbenzenesulfonate,
bis(4-tert-butoxycarbonylmethyloxyphenyl)(3-dimethylamino-phenyl)sulfonium benzenesulfonate,
(4-tert-butoxycarbonylmethyloxyphenyl)bis(3-dimethylamino-phenyl)sulfonium benzenesulfonate, etc.

Examples of sulfonium salts having a 4-(2-picolyloxy)-phenyl group as the nitrogenous aromatic group include:
tris(4-(2-picolyloxy)phenyl)sulfonium p-toluenesulfonate,
bis(4-tert-butoxyphenyl)(4-(2-picolyloxy)phenyl)sulfonium p-toluenesulfonate,
(4-tert-butoxyphenyl)bis(4-(2-picolyloxy)phenyl)sulfonium p-toluenesulfonate,
bis(4-tert-butoxycarbonylmethyloxyphenyl)(4-(2-picolyloxy)phenyl)sulfonium p-toluenesulfonate,
(4-tert-butoxycarbonylmethyloxyphenyl)bis(4-(2-picolyloxy)phenyl)sulfonium p-toluenesulfonate,
bis(4-(1-ethoxyethyloxy)phenyl)(4-(2-picolyloxy)phenyl)-sulfonium p-toluenesulfonate,
(4-(1-ethoxyethyloxy)phenyl)bis(4-(2-picolyloxy)phenyl)-sulfonium p-toluenesulfonate,
bis(4-tetrahydropyranyloxyphenyl)(4-(2-picolyloxy) phenyl)-sulfonium p-toluenesulfonate,
(4-tetrahydrofuranyloxyphenyl)bis(4-(2-picolyloxy) phenyl)-sulfonium p-toluenesulfonate,
tris(4-(2-picolyloxy)phenyl)sulfonium p-ethylbenzene-sulfonate,
tris(4-(2-picolyloxy)phenyl)sulfonium 2,4-dimethylbenzene-sulfonate,
bis(4-tert-butoxyphenyl)(4-(2-picolyloxy)phenyl)sulfonium 2,4-dimethylbenzenesulfonate,
(4-tert-butoxyphenyl)bis(4-(2-picolyloxy)phenyl)sulfonium 2,4-dimethylbenzenesulfonate,
(4-tert-butoxyphenyl)bis(4-(2-picolyloxy)phenyl)sulfonium p-tert-butylbenzenesulfonate,
bis(4-tert-butoxycarbonylmethyloxyphenyl)(4-(2-picolyloxy)phenyl)sulfonium 2,5-dimethylbenzenesulfonate,
(4-tert-butoxycarbonylmethyloxyphenyl)bis(4-(2-picolyloxy)phenyl)sulfonium n-octylbenzenesulfonate,
tris(4-(2-picolyloxy)phenyl)sulfonium p-tert-butylbenzene-sulfonate,
bis(4-tert-butoxyphenyl)(4-(2-picolyloxy)phenyl)sulfonium benzenesulfonate,
(4-tert-butoxyphenyl)bis(4-(2-picolyloxy)phenyl)sulfonium benzenesulfonate,
bis(4-tert-butoxycarbonylmethyloxyphenyl)(4-(2-picolyloxy)phenyl)sulfonium benzenesulfonate,
(4-tert-butoxycarbonylmethyloxyphenyl)bis(4-(2-picolyloxy)phenyl)sulfonium benzenesulfonate, etc.

Examples of sulfonium salts having a 4-(4-picolyloxy)-phenyl group as the nitrogenous aromatic group include:
tris(4-(4-picolyloxy)phenyl)sulfonium p-toluenesulfonate,
bis(4-tert-butoxyphenyl)(4-(4-picolyloxy)phenyl)sulfonium p-toluenesulfonate,
(4-tert-butoxyphenyl)bis(4-(4-picolyloxy)phenyl)sulfonium p-toluenesulfonate,
bis(4-tert-butoxycarbonylmethyloxyphenyl)(4-(4-picolyloxy)-phenyl)sulfonium p-toluenesulfonate,
(4-tert-butoxycarbonylmethyloxyphenyl)bis(4-(4-picolyloxy)-phenyl)sulfonium p-toluenesulfonate, bis(4-(1-ethoxyethyloxy)phenyl)(4-(4-picolyloxy)phenyl)-
sulfonium p-toluenesulfonate,
(4-(1-ethoxyethyloxy)phenyl)bis(4-(4-picolyloxy)phenyl)-
sulfonium p-toluenesulfonate,
bis(4-tetrahydropyranyloxyphenyl)(4-(4-picolyloxy)
phenyl)-sulfonium p-toluenesulfonate,
(4-tetrahydrofuranyloxyphenyl)bis(4-(4-picolyloxy)phenyl)
-sulfonium p-toluenesulfonate,
tris(4-(4-picolyloxy)phenyl)sulfonium p-ethylbenzene-
sulfonate,
tris(4-(4-picolyloxy)phenyl)sulfonium 2,4-
dimethylbenzene-sulfonate,
bis(4-tert-butoxyphenyl)(4-(4-picolyloxy)phenyl)sulfonium
2,4-dimethylbenzenesulfonate,
(4-tert-butoxyphenyl)bis(4-(4-picolyloxy)phenyl)sulfonium
2,4-dimethylbenzenesulfonate,
(4-tert-butoxycarbonylmethyloxyphenyl)bis(4-(4-
picolyloxy)-phenyl)sulfonium 2,4-
dimethylbenzenesulfonate,
bis(4-tert-butoxyphenyl)(4-(4-picolyloxy)phenyl)sulfonium
p-tert-butylbenzenesulfonate,
(4-tert-butoxyphenyl)bis(4-(4-picolyloxy)phenyl)sulfonium
p-tert-butylbenzenesulfonate,
bis(4-tert-butoxycarbonylmethyloxyphenyl)(4-(4-
picolyloxy)-phenyl)sulfonium 2,5-
dimethylbenzenesulfonate,
(4-tert-butoxycarbonylmethyloxyphenyl)bis(4-(4-
picolyloxy)-phenyl)sulfonium n-octylbenzenesulfonate,
tris(4-(4-picolyloxy)phenyl)sulfonium p-tert-butylbenzene-
sulfonate,
bis(4-tert-butoxyphenyl)(4-(4-picolyloxy)phenyl)sulfonium
benzenesulfonate,
(4-tert-butoxyphenyl)bis(4-(4-picolyloxy)phenyl)sulfonium
p-tert-butylbenzenesulfonate,
bis(4-tert-butoxycarbonylmethyloxyphenyl)(4-(4-
picolyloxy)-phenyl)sulfonium benzenesulfonate,
(4-tert-butoxycarbonylmethyloxyphenyl)bis(4-(4-
picolyloxy)-phenyl)sulfonium benzenesulfonate, etc.

Examples of sulfonium salts having a 3-(4-picolyloxy)-
phenyl group as the nitrogenous aromatic group include:
tris(3-(4-picolyloxy)phenyl)sulfonium p-toluenesulfonate,
bis(4-tert-butoxyphenyl)(3-(4-picolyloxy)phenyl)sulfonium
p-toluenesulfonate,
(4-tert-butoxyphenyl)bis(3-(4-picolyloxy)phenyl)sulfonium
p-toluenesulfonate,
bis(4-tert-butoxycarbonylmethyloxyphenyl)(3-(4-
picolyloxy)-phenyl)sulfonium p-toluenesulfonate,
(4-tert-butoxycarbonylmethyloxyphenyl)bis(3-(4-
picolyloxy)-phenyl)sulfonium p-toluenesulfonate,
bis(4-(1-ethoxyethyloxy)phenyl)(3-(4-picolyloxy)phenyl)-
sulfonium p-toluenesulfonate,
(4-(1-ethoxyethyloxy)phenyl)bis(3-(4-picolyloxy)phenyl)-
sulfonium p-toluenesulfonate,
bis(4-tetrahydropyranyloxyphenyl)(3-(4-picolyloxy)
phenyl)-sulfonium p-toluenesulfonate,
(4-tetrahydrofuranyloxyphenyl)bis(3-(4-picolyloxy)
phenyl)-sulfonium p-toluenesulfonate,
tris(3-(4-picolyloxy)phenyl)sulfonium p-ethylbenzene-
sulfonate,
tris(3-(4-picolyloxy)phenyl)sulfonium 2,4-
dimethylbenzene-sulfonate,
bis(4-tert-butoxyphenyl)(3-(4-picolyloxy)phenyl)sulfonium
2,4-dimethylbenzenesulfonate,
(4-tert-butoxyphenyl)bis(3-(4-picolyloxy)phenyl)sulfonium
2,4-dimethylbenzenesulfonate,
bis(4-tert-butoxycarbonylmethyloxyphenyl)(3-(4-
picolyloxy)-phenyl)sulfonium 2,4-
dimethylbenzenesulfonate, (4-tert-butoxycarbonylmethyloxyphenyl)bis(3-(4-
picolyloxy)-phenyl)sulfonium 2,4-
dimethylbenzenesulfonate,
(4-tert-butoxycarbonylmethyloxyphenyl)bis(3-(4-
picolyloxy)-phenyl)sulfonium n-octylbenzenesulfonate,
tris(3-(4-picolyloxy)phenyl)sulfonium benzenesulfonate,
bis(4-tert-butoxyphenyl)(3-(4-picolyloxy)phenyl)sulfonium
benzenesulfonate,
(4-tert-butoxycarbonylmethyloxyphenyl)bis(3-(4-
picolyloxy)phenyl)sulfonium benzenesulfonate, etc.

Examples of sulfonium salts having a 3-(2-picolyloxy)-
phenyl group as the nitrogenous aromatic group include:
tris(3-(2-picolyloxy)phenyl)sulfonium p-toluenesulfonate,
bis(4-tert-butoxyphenyl)(3-(2-picolyloxy)phenyl)sulfonium
p-toluenesulfonate,
(4-tert-butoxyphenyl)bis(3-(2-picolyloxy)phenyl)sulfonium
p-toluenesulfonate,
bis(4-tert-butoxycarbonylmethyloxyphenyl)(3-(2-
picolyloxy)-phenyl)sulfonium p-toluenesulfonate,
(4-tert-butoxycarbonylmethyloxyphenyl)bis(3-(2-
picolyloxy)-phenyl)sulfonium p-toluenesulfonate,
bis(4-(1-ethoxyethyloxy)phenyl)(3-(2-picolyloxy)phenyl)-
sulfonium p-toluenesulfonate,
(4-(1-ethoxyethyloxy)phenyl)bis(3-(2-picolyloxy)phenyl)-
sulfonium p-toluenesulfonate,
bis(4-tetrahydropyranyloxyphenyl)(3-(2-picolyloxy)
phenyl)-sulfonium p-toluenesulfonate,
(4-tetrahydrofuranyloxyphenyl)bis(3-(2-picolyloxy)
phenyl)-sulfonium p-toluenesulfonate,
tris(3-(2-picolyloxy)phenyl)sulfonium p-ethylbenzene-
sulfonate,
tris(3-(2-picolyloxy)phenyl)sulfonium 2,4-
dimethylbenzene-sulfonate,
bis(4-tert-butoxyphenyl)(3-(2-picolyloxy)phenyl)sulfonium
2,4-dimethylbenzenesulfonate,
(4-tert-butoxycarbonylmethyloxyphenyl)bis(3-(2-
picolyloxy)-phenyl)sulfonium 2,4-
dimethylbenzenesulfonate,
(3-tert-butoxyphenyl)bis(3-(2-picolyloxy)phenyl)sulfonium
p-tert-butylbenzenesulfonate,
bis(4-tert-butoxycarbonylmethyloxyphenyl)(3-(2-
picolyloxy)-phenyl)sulfonium 4-tert-
butylbenzenesulfonate,
(4-tert-butoxycarbonylmethyloxyphenyl)bis(3-(2-
picolyloxy)-phenyl)sulfonium n-octylbenzenesulfonate,
tris(3-(2-picolyloxy)phenyl)sulfonium benzenesulfonate,
bis(4-tert-butoxyphenyl)(3-(2-picolyloxy)phenyl)sulfonium
benzenesulfonate,
(4-tert-butoxycarbonylmethyloxyphenyl)bis(3-(2-
picolyloxy)-phenyl)sulfonium benzenesulfonate, etc.

Examples of sulfonium salts having a pyridin-3-yl group
as the nitrogenous aromatic group include:
tris(pyridin-3-yl)sulfonium p-toluenesulfonate,
bis(4-tert-butoxyphenyl)(pyridin-3-yl)sulfonium
p-toluenesulfonate,
(4-tert-butoxyphenyl)bis(pyridin-3-yl)sulfonium
p-toluenesulfonate,
bis(4-tert-butoxycarbonylmethyloxyphenyl)(pyridin-3-yl)-
sulfonium p-toluenesulfonate,
(4-tert-butoxycarbonylmethyloxyphenyl)bis(pyridin-3-yl)-
sulfonium p-toluenesulfonate,
bis(4-(1-ethoxyethyloxy)phenyl)(pyridin-3-yl)sulfonium
p-toluenesulfonate,
(4-(1-ethoxyethyloxy)phenyl)bis(pyridin-3-yl)sulfonium
p-toluenesulfonate,
bis(4-tetrahydropyranyloxyphenyl)(pyridin-3-yl)sulfonium
p-toluenesulfonate, (4-tetrahydrofuranyloxyphenyl)bis(pyridin-3-yl)sulfonium p-toluenesulfonate,
tris(pyridin-3-yl)sulfonium p-ethylbenzenesulfonate,
tris(pyridin-3-yl)sulfonium 2,4-dimethylbenzenesulfonate,
bis(4-tert-butoxyphenyl)(pyridin-3-yl)sulfonium 2,4-dimethyl-benzenesulfonate,
(4-tert-butoxycarbonylmethyloxyphenyl)bis(pyridin-3-yl)-sulfonium 2,4-dimethylbenzenesulfonate,
(4-tert-butoxyphenyl)bis(pyridin-3-yl)sulfonium p-tert-butylbenzenesulfonate,
(4-tert-butoxycarbonylmethyloxyphenyl)bis(pyridin-3-yl)-sulfonium n-octylbenzenesulfonate,
tris(pyridin-3-yl)sulfonium benzenesulfonate,
bis(4-tert-butoxyphenyl)(pyridin-3-yl)sulfonium benzenesulfonate,
(4-tert-butoxycarbonylmethyloxyphenyl)bis(pyridin-3-yl)-sulfonium benzenesulfonate, etc.

Examples of sulfonium salts having a pyridin-2-yl group as the nitrogenous aromatic group include:
tris(pyridin-2-yl)sulfonium p-toluenesulfonate,
bis(4-tert-butoxyphenyl)(pyridin-2-yl)sulfonium p-toluenesulfonate,
(4-tert-butoxyphenyl)bis(pyridin-2-yl)sulfonium p-toluenesulfonate,
bis(4-tert-butoxycarbonylmethyloxyphenyl)(pyridin-2-yl)-sulfonium p-toluenesulfonate,
(4-tert-butoxycarbonylmethyloxyphenyl)bis(pyridin-2-yl)-sulfonium p-toluenesulfonate,
bis(4-(1-ethoxyethyloxy)phenyl)(pyridin-2-yl)sulfonium p-toluenesulfonate,
(4-(1-ethoxyethyloxy)phenyl)bis(pyridin-2-yl)sulfonium p-toluenesulfonate,
bis(4-tetrahydropyranyloxyphenyl)(pyridin-2-yl)sulfonium p-toluenesulfonate,
(4-tetrahydrofuranyloxyphenyl)bis(pyridin-2-yl)sulfonium p-toluenesulfonate,
tris(pyridin-2-yl)sulfonium p-ethylbenzenesulfonate,
tris(pyridin-2-yl)sulfonium 2,4-dimethylbenzenesulfonate,
bis(4-tert-butoxyphenyl)(pyridin-2-yl)sulfonium 2,4-dimethylbenzenesulfonate,
(4-tert-butoxyphenyl)bis(pyridin-2-yl)sulfonium 2,4-dimethylbenzenesulfonate,
bis(3-tert-butoxycarbonylmethyloxyphenyl)(pyridin-2-yl)-sulfonium 2,4-dimethylbenzenesulfonate,
(4-tert-butoxycarbonylmethyloxyphenyl)bis(pyridin-2-yl)-sulfonium 2,4-dimethylbenzenesulfonate,
(4-tert-butoxyphenyl)bis(pyridin-2-yl)sulfonium p-tert-butylbenzenesulfonate,
(4-tert-butoxycarbonylmethyloxyphenyl)bis(pyridin-2-yl)-sulfonium n-octylbenzenesulfonate,
tris(pyridin-2-yl)sulfonium benzenesulfonate,
bis(4-tert-butoxyphenyl)(pyridin-2-yl)sulfonium benzenesulfonate,
(4-tert-butoxycarbonylmethyloxyphenyl)bis(pyridin-2-yl)-sulfonium benzenesulfonate, etc.

The sulfonium salt of formula (1) according to the invention can be synthesized according to the following route. A substituted or unsubstituted bisaryl sulfoxide of the general formula (2) is reacted with a trialkylsilylarylsulfonate of the general formula (3) in an organic solvent and further with a Grignard reagent of the general formula (4) which has been prepared in an organic solvent such as THF.

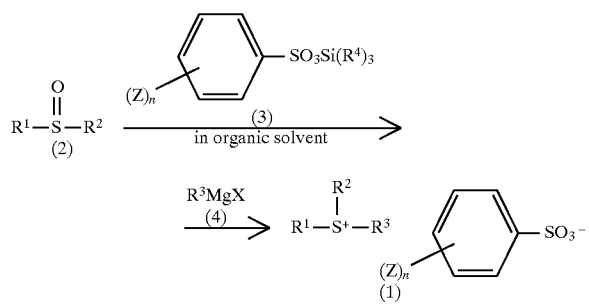

In the formulae, $R^1$ to $R^4$, Z, X, and n are as defined above.

Examples of the substituted or unsubstituted bisaryl sulfoxide of formula (2) are given below.

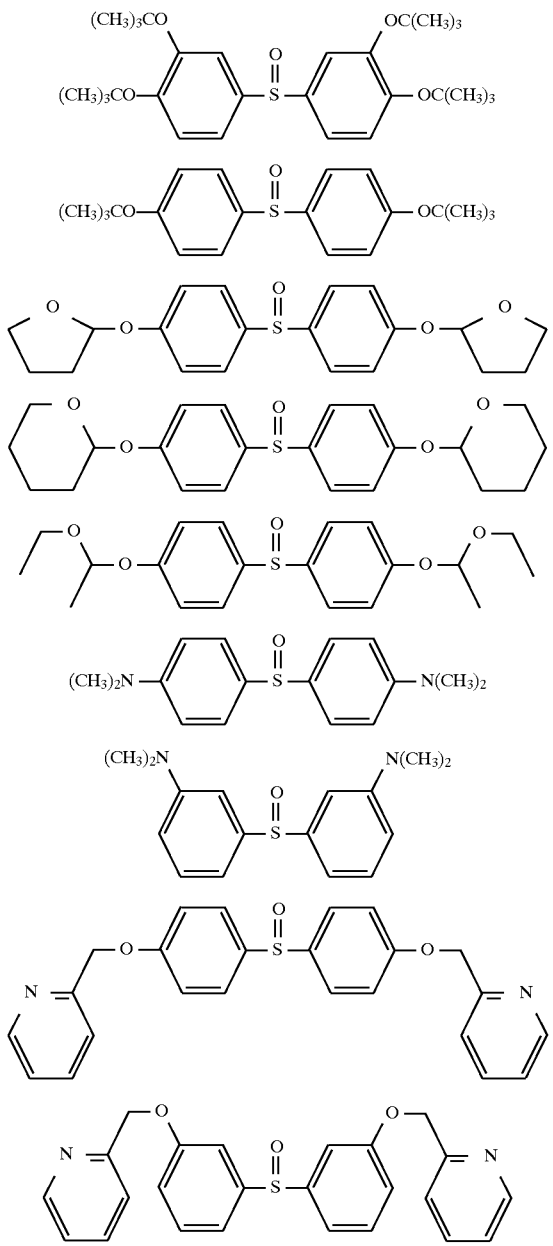

-continued

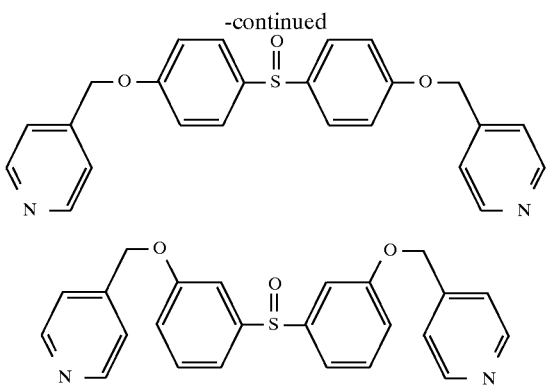

Besides, there can be used any of bisaryl sulfoxides possessing a substituent which can be present stable with respect to trialkylsilylarylsulfonates and Grignard reagents and an aromatic group having an acid labile group or an aromatic group containing nitrogen.

It is to be noted that when sulfoxides having tert-butoxy groups at 2- and 2'-positions such as bis(2,4-di-tert-butoxyphenyl) sulfoxide are used as the sulfoxide of formula (2), few end compounds can be obtained because of steric hindrance. The same applies when sulfoxides having tetrahydropyranyloxy groups at 2- and 2'-positions are used. Synthesis is possible with sulfoxides having only one 2-substituted phenyl group.

Substituted bisaryl sulfoxides can also be synthesized by reacting a Grignard reagent of formula (4) with thionyl chloride.

For the trialkylsilylarylsulfonate used herein, the alkyl groups contained therein may be identical or different and those alkyl groups having 1 to 4 carbon atoms are preferred. Trimethylsilyl, triethylsilyl, and tert-butyl-dimethylsilyl groups are especially preferred. Examples of the trialkylsilylarylsulfonate include trimethylsilylbenzene-sulfonate, triethylsilylbenzenesulfonate, tert-butyldimethylsilylbenzenesulfonate, trimethylsilyl-p-toluenesulfonate, triethylsilyl-p-toluenesulfonate, tert-butyldimethylsilyl-p-toluenesulfonate, trimethylsilyl-p-ethylbenzenesulfonate, triethylsilyl-p-ethylbenzenesulfonate, tert-butyldimethylsilyl-p-ethylbenzenesulfonate, trimethylsilyl-2,4-dimethylbenzenesulfonate, triethylsilyl-2,4-dimethylbenzenesulfonate, tert-butyldimethylsilyl-2,4-dimethylbenzenesulfonate, trimethylsilyl-p-tert-butylbenzenesulfonate, triethylsilyl-p-tert-butylbenzenesulfonate, tert-butyldimethylsilyl-p-tert-butylbenzenesulfonate, and trimethylsilyloctylbenzenesulfonate.

Examples of the aryl Grignard reagent of formula (4) include phenyl Grignard, tert-butoxyphenyl Grignard, tetrahydropyranyloxyphenyl Grignard, tetrahydrofuranyloxyphenyl Grignard, 1-ethoxyethyloxyphenyl Grignard, dimethyl-aminophenyl Grignard, and pyridinyl Grignard although any of Grignard reagents which are present stable may be used. Aryl Grignard reagents containing nitrogen or an acid labile group are desired.

In the above-mentioned reaction, various functional substituent groups such as nitrogenous aromatic groups and aromatic groups having an acid labile group can be introduced into the sulfonium salt of formula (1) by changing a combination of the sulfoxide derivative and the aryl Grignard reagent.

In the above-mentioned reactions for the synthesis of the sulfonium salt, it is preferred to mix 1 mol of the sulfoxide of formula (2) with 1 to 5 mol, especially 2 to 3 mol of the trialkylsilylarylsulfonate of formula (3) and to add 1 to 5 mol, especially 2 to 3 mol of the Grignard reagent of formula (4) to 1 mol of the sulfoxide of formula (2). These reactions are desirably carried out in an organic solvent such as THF and methylene chloride in the presence of an organic base such as triethylamine and pyridine in order to prevent elimination of an acid labile group by a trace amount of acidic impurities in the trialkylsilylarylsulfonate of formula (3). It is noted that where an aromatic group having an acid labile group is contained, a reaction temperature of 0° to 10° C. is preferred although reaction conditions are not critical.

Furthermore, in the practice of the invention, a sulfonium salt of formula (1) having a nitrogenous aromatic group and a substituted or unsubstituted arylsulfonate anion can be synthesized from a sulfonium salt having an acid labile group by deblocking the acid labile group of the sulfonium salt with a substituted or unsubstituted arylsulfonic acid and substituting a nitrogenous substituent such as halogenated methylpyridine for the hydrogen atom of a phenolic hydroxyl group by a conventional method. More particularly, as shown in the following reaction scheme, tris(4-tert-butoxyphenyl)sulfonium p-toluenesulfonate represented by formula (5) is deblocked in an organic solvent such as methanol using p-toluenesulfonic acid of formula (6), and then reacted with 4-chloromethylpyridine of formula (7) under basic conditions, thereby synthesizing a sulfonium salt of formula (1a) having a p-toluenesulfonate anion and a 4-(4-picolyloxy)phenyl as a nitrogenous group.

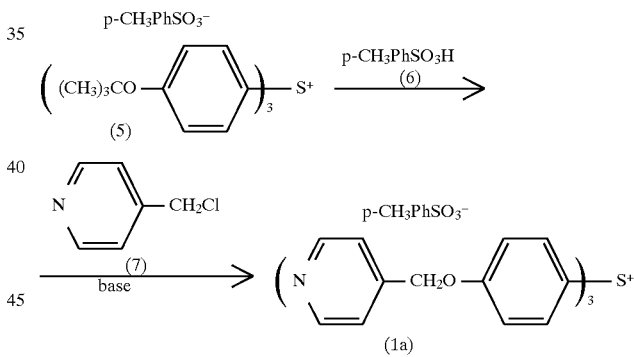

In the formulae, Ph stands for a phenylene group.

Also in the case of a nitrogenous sulfonium salt of formula (1) having an acid labile group, the acid labile group such as a tert-butoxyphenyl group can be deblocked and then replaced by another acid labile group such as a tert-butoxycarbonyl and tert-butoxycarbonylmethyl group. More particularly, as shown in the following reaction scheme, a tert-butoxy group of (4-tert-butoxyphenyl)bis(4-dimethylaminophenyl)sulfonium p-toluenesulfonate of formula (1b) is deblocked with p-toluenesulfonic acid of formula (6) and then reacted with tert-butyl chloroacetate of formula (8) under basic conditions, thereby synthesizing a sulfonium salt of formula (1c) having a 4-tert-butoxycarbonylmethyloxyphenyl group and a dimethylaminophenyl group.

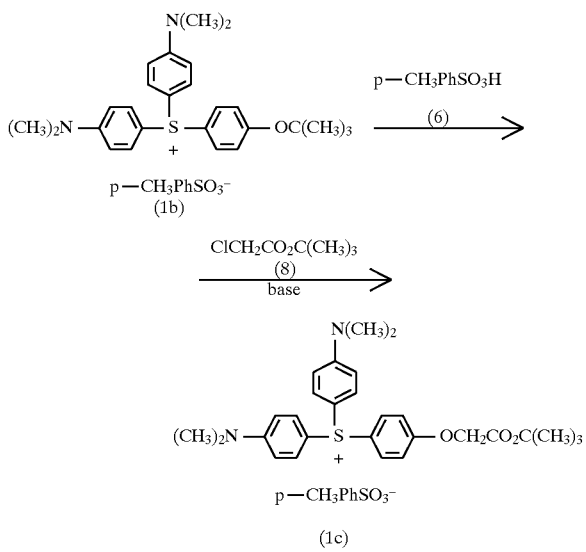

In a second aspect, the present invention provides a chemically amplified, positive working resist composition comprising the sulfonium salt of formula (1). The resist composition may be formulated as either a two component chemically amplified, positive resist composition (organic solvent/alkali soluble resin/photoacid generator) or a three component chemically amplified, positive resist composition (organic solvent/alkali soluble resin/photoacid generator/dissolution inhibitor), with the three component system being preferred.

Typical embodiments of the resist composition of the invention are shown below.

Embodiment (i) is a chemically amplified positive resist composition comprising
(A) an organic solvent,
(B) an alkali soluble resin,
(C) a dissolution inhibitor having an acid labile group,
(D) a sulfonium salt of formula (1), and
(E) a photoacid generator other than the sulfonium salt of formula (1).

Embodiment (ii) is a chemically amplified positive resist composition comprising
(A) an organic solvent,
(B) an alkali soluble resin,
(C) a dissolution inhibitor having an acid labile group,
(D) a sulfonium salt of formula (1), and
(F) an onium salt of the following general formula (9):

$(R^5)_a MY$ (9)

wherein $R^5$ is independently selected from substituted or unsubstituted aromatic and aliphatic groups, M is sulfonium or iodonium, Y is a substituted or unsubstituted alkylsulfonate or arylsulfonate, and letter a is equal to 2 or 3.

Embodiment (iii) is a chemically amplified positive resist composition comprising
(A) an organic solvent,
(B) an alkali soluble resin,
(C) a dissolution inhibitor having an acid labile group, and
(D) a sulfonium salt of formula (1).

Embodiment (iv) is a chemically amplified positive resist composition comprising
(A) an organic solvent,
(B) an alkali soluble resin,
(D) a sulfonium salt of formula (1), and
(E) a photoacid generator other than the sulfonium salt of formula (1).

Embodiment (v) is a chemically amplified positive resist composition comprising
(A) an organic solvent,
(B) an alkali soluble resin,
(D) a sulfonium salt of formula (1), and
(F) an onium salt of formula (9).

Embodiment (vi) is a chemically amplified positive resist composition comprising
(A) an organic solvent,
(B) an alkali soluble resin, and
(D) a sulfonium salt of formula (1).

Examples of organic solvent (A) include ketones such as cyclohexanone and methyl amyl ketone; alcohols such as 3-methoxybutanol, 3-methyl-3-methoxybutanol, 1-methoxy-2-propanol and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; and esters such as propylene glycol monomethyl ether acetate, propylene glycol monoethyl ether acetate, ethyl lactate, ethyl pyruvate, butyl acetate, methyl 3-methoxypropionate and ethyl 3-ethoxypropionate, alone or in admixture of two or more. Among these, 1-ethoxy-2-propanol is preferred because the photoacid generator as a resist component is most soluble therein.

Examples of alkali soluble resin (B) as the base resin include polyhydroxystyrene and derivatives thereof. Preferred are those polyhydroxystyrene derivatives wherein hydrogen atoms of some OH groups of polyhydroxystyrene are replaced by acid labile groups and hydroxystyrene copolymers. In the former, examples of the acid labile group used therein include substituents of tert-butyl derivatives such as tert-butyl, tert-butoxycarbonyl, and tert-butoxycarbonyl-methyl groups; normal or branched chain acetal groups such as 1-ethoxyethyl, 1-propoxyethyl, 1-n-butoxyethyl, 1-isobutoxyethyl, 1-tert-butoxyethyl, and 1-tert-amyloxyethyl groups; and cyclic acetal groups such as tetrahydrofuranyl, tetrahydropyranyl, and 2-methoxytetrahydropyranyl groups. These acid labile groups may be used alone or in admixture of two or more at the same time. Included in the hydroxystyrene copolymers are copolymers of hydroxystyrene and styrene, copolymers of hydroxystyrene and tert-butyl acrylate, copolymers of hydroxystyrene and tert-butyl methacrylate, copolymers of hydroxystyrene and maleic anhydride, and copolymers of hydroxystyrene and di-tert-butyl maleate. The polyhydroxystyrene derivatives should preferably have a weight average molecular weight of about 3,000 to about 100,000. Film formability and resolution would be poor with Mw of less than 3,000 whereas resolution would be poor with Mw of more than 100,000.

Dissolution inhibitor (C) should have at least one group which is decomposable with an acid (acid labile group) in a molecule and may be either a low molecular weight compound or a polymer. Any of well-known dissolution inhibitors may be used. Exemplary low molecular weight compounds include bisphenol A derivatives and carbonate derivatives. Preferred are those bisphenol A derivatives wherein the hydrogen atom of the hydroxyl group of bisphenol A is replaced by tert-butyl derivative substituents such as tert-butoxy, tert-butoxycarbonyl, and tert-butoxycarbonylmethyl groups; normal or branched chain acetal groups such as 1-ethoxyethyl, 1-propoxyethyl, 1-n-butoxyethyl, 1-isobutoxy-ethyl, 1-tert-butoxyethyl, and 1-tert-amyloxyethyl groups; and cyclic acetal groups such as tetrahydrofuranyl, tetrahydropyranyl, and 2-methoxytetrahydropyranyl groups. Also preferred are tert-butyl 4,4'-di(4-hydroxyphenyl)-valerate derivatives wherein the hydrogen atom of the hydroxyl group is replaced by tert-butyl derivative substituents such as tert-butoxy, tert-butoxycarbonyl, and tert-butoxycarbonylmethyl groups; normal or branched chain acetal groups such as 1-ethoxyethyl, 1-propoxyethyl, 1-n-butoxyethyl, 1-isobutoxyethyl, 1-tert-butoxyethyl, and 1-tert-amyloxyethyl groups; and cyclic acetal groups such as tetrahydrofuranyl and tetrahydropyranyl groups. These acid labile groups may be contained alone or in admixture of two or more.

Examples of the polymeric dissolution inhibitor include copolymers of p-butoxystyrene and t-butyl acrylate, and copolymers of p-butoxystyrene and maleic anhydride, with those copolymers having a weight average molecular weight of about 500 to about 10,000 being preferred.

According to the invention, the sulfonium salt of formula (1) is blended as photoacid generator (D). If necessary, a mixture of sulfonium salts of formula (1) possessing different nitrogenous aromatic groups, different aromatic groups having an acid labile group or different arylsulfonate anions may be used.

Also if necessary, another photoacid generator may be blended as component (E) or (F) in addition to the sulfonium salt of formula (1). The other photoacid generators which can be used as component (E) or (F) include onium salts, oxime sulfonic acid derivatives, 2,6-dinitrobenzylsulfonic acid derivatives, diazonaphthoquinone sulfonate derivatives, 2,4-bistrichloromethyl-6-aryl-1,3,5-triazine derivatives, aryl sulfonic acid ester derivatives, pyrogallol sulfonic acid ester derivatives, N-sulfonyloxyimide derivatives such as N-trifluoromethanesulfonyloxyphthalide and N-(10(+)-camphorsulfonyl)oxynaphthalide, α, α'-bisarylsulfonyl-diazomethane derivatives, α, α'-bisalkylsulfonyldiazomethane derivatives, benzoinsulfonate derivatives, and β-ketosulfon derivatives. Preferred are onium salts of the following general formula (9):

$$(R^5)_a MY \qquad (9)$$

wherein $R^5$ is independently selected from substituted or unsubstituted aromatic and aliphatic groups, M is sulfonium or iodonium, Y is a substituted or unsubstituted alkylsulfonate or arylsulfonate, and letter a is equal to 2 or 3. Exemplary aromatic groups represented by $R^5$ are a phenyl group, alkylphenyl and alkoxyphenyl groups as described for formula (1), aromatic groups having an acid labile group, and aliphatic groups such as alkyl and 2-oxoalkyl groups.

Illustrative examples of the onium salt of formula (9) are given by the following iodonium and sulfonium salts.

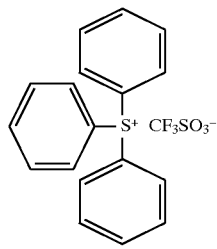

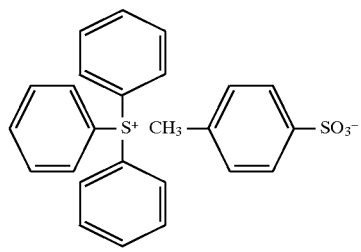

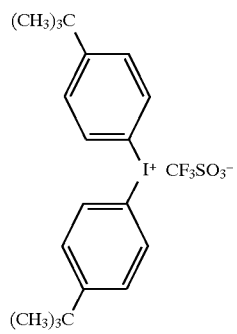

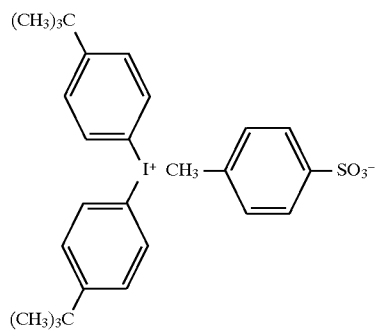

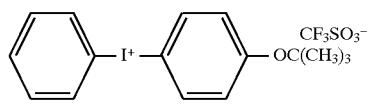

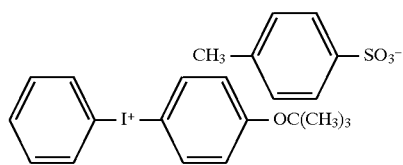

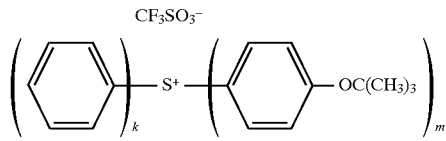

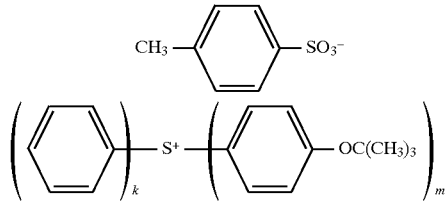

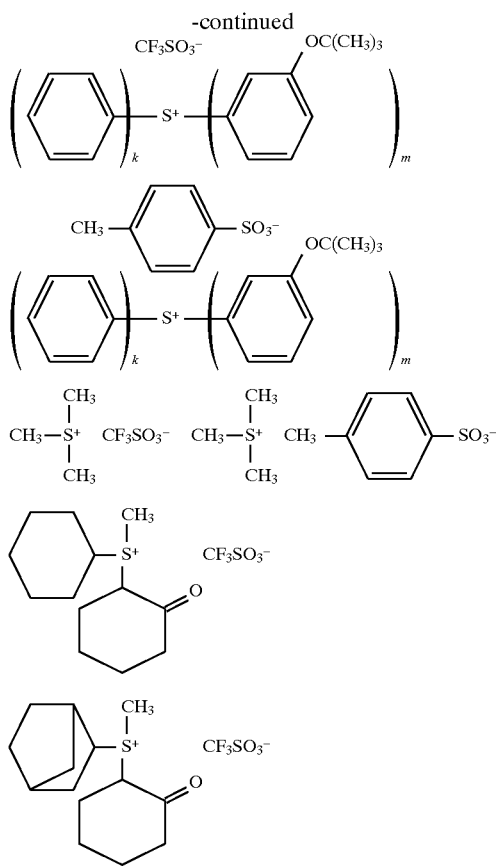

Note that k is an integer of 0 to 2, m is an integer of 1 to 3, and the sum of k and m is equal to 3.

Preferably the two-component resist composition is comprised of, in parts by weight, (A) about 150 to 700 parts, more preferably 250 to 500 parts of an organic solvent, and (B) about 70 to 90 parts, more preferably 75 to 85 parts of an alkali soluble resin. The three-component resist composition further includes (C) about 5 to 40 parts, more preferably 10 to 25 parts of a dissolution inhibitor having an acid labile group. It is noted that the amount of other components to be described later is based on the amounts of components (A) to (C) described just above.

As component (D), about 0.5 to 15 parts, especially 2 to 8 parts of a sulfonium salt of formula (1) is preferably blended. With less than 0.5 part of the sulfonium salt, the amount of acid generated upon exposure would be too small to ensure sensitivity and resolution. With more than 15 parts of the sulfonium salt, a resist film would have low transmittance, sensitivity and resolution.

The other photoacid generator (E) or (F), if blended, is preferably used in amounts of about 0.5 to 15 parts, more preferably 2 to 10 parts. In this case, the sulfonium salt of formula (1) as component (D) is preferably used in amounts of 0.001 to 10 parts, especially 0.01 to 5 parts. The total of component (D) and component (E) or (F) is desirably 0.025 to 15 parts, especially 0.5 to 8 parts.

The amounts of these photoacid generators blended vary depending on the reflectance and alkalinity of a substrate used and the concentration of basic compounds in air. Where the substrate has a lower reflectance, a smaller amount of photoacid generator is blended to increase the transmittance of a resist film. Where the substrate has a higher reflectance so that standing wave or profile degradation due to irregular reflection on a stepped substrate is found, and where the influence of basic compounds is substantial, the amount of the sulfonium salt of formula (1) is increased to reduce such influence.

The resist composition of the invention may further contain various additives, for example, carboxylic acid derivatives and nitrogenous compounds for improving PED stability, surfactants for facilitating coating, and light-absorbing agents for reducing irregular reflection from the substrate.

Exemplary carboxylic acid derivatives include 4-hydroxyphenylacetic acid, 3-hydroxyphenylacetic acid, 2-hydroxyphenylacetic acid, 3-(4-hydroxyphenyl)propionic acid, 3-(2-hydroxyphenyl)propionic acid, 2,5-dihydroxyphenylacetic acid, 3,4-dihydroxyphenylacetic acid, 1,2-phenylenediacetic acid, 1,3-phenylenediacetic acid, 1,4-phenylenediacetic acid, 1,2-phenylenedioxydiacetic acid, 1,4-phenylenedipropanoic acid, benzoic acid, 4,4-bis(4-hydroxyphenyl)valeric acid, 4-tert-butoxyphenylacetic acid, 4-(4-hydroxyphenyl)butyric acid, 3,4-dihydroxymandelic acid, and 4-hydroxymandelic acid. The carboxylic acid derivative is preferably blended in an amount of about 0.1 to 15 parts, especially about 1 to 10 parts in the resist composition of the invention.

The nitrogenous compounds used herein include primary, secondary and tertiary aliphatic amines, mixed amines, nitrogenous compounds having an aromatic or heterocyclic ring, nitrogenous compounds having a carboxyl group, nitrogenous compounds having a sulfonyl group, nitrogenous compounds having a hydroxyl group, nitrogenous compounds having a hydroxylphenyl group, alcoholic nitrogenous compounds, and amide derivatives. More illustratively, examples of the primary aliphatic amine include ammonia, methylamine, ethylamine, propylamine, butylamine, pentylamine, amylamine, hexylamine, heptylamine, octylamine, nonylamine, decylamine, laurylamine, cetylamine, methylenediamine, ethylenediamine, and tetraethylene diamine. Examples of the secondary aliphatic amines include dimethylamine, diethylamine, dipropylamine, dibutylamine, dipentylamine, diamylamine, dihexylamine, diheptylamine, dioctylamine, dinonylamine, didecylamine, dimethylmethylene-diamine, dimethylethylenediamine, and dimethyltetraethylene diamine. Examples of the tertiary aliphatic amines include trimethylamine, triethylamine, tripropylamine, tributylamine, tripentylamine, trihexylamine, triheptylamine, trioctylamine, tetramethylmethylenediamine, tetramethylethylenediamine, and tetramethyltetraethylenediamine.

Typical mixed amines are dimethylethylamine, methylethylpropylamine, etc.

Examples of the nitrogenous compound having an aromatic or heterocyclic ring include benzylamine, phenethylamine, benzyldimethylamine, aniline derivatives (e.g., aniline, N-methylaniline, N,N-dimethylaniline, o-toluidine, m-toluidine, p-toluidine, 2,4-lutidine, nitroaniline, and dinitroaniline), quinoline, isoquinoline, o-aminobenzoic acid, m-aminobenzoic acid, p-aminobenzoic acid, 1,2-phenylenediamine, 1,3-phenylenediamine, 1,4-phenylenediamine, naphthylamine, diaminonaphthalene, pyrrole derivatives (e.g., pyrrole, methylpyrrole, dimethylpyrrole, and N-methylpyrrole), imidazole derivatives (e.g., imidazole, 4-methylimidazole, and 4-methyl-2-phenylimidazole), oxazole derivatives, thiazole derivatives, pyrazole derivatives, pyrrolidine derivatives (e.g., pyrrolidine, N-methylpyrrolidine, and N-methylpyrrolidone), pyrroline derivatives, pyridine derivatives (e.g., pyridine, α-picoline, β-picoline, γ-picoline, ethylpyridine, propylpyridine, butylpyridine, 5-butyl-2- methylpyridine, trimethylpyridine, triethylpyridine, phenylpyridine, 3-methyl-2-phenylpyridine, tert-butylpyridine, diphenylpyridine, benzylpyridine, methoxypyridine, butoxypyridine, dimethoxypyridine, 1-methyl-2-pyridone, 4-pyrrolidinylpyridone, 1-methyl-4-phenylpyridine, and 2-(1-ethylpropyl)pyridine), piperidine derivatives, pyrimidine derivatives, purine derivatives, quinoline derivatives, carbazole derivatives, indole derivatives, nicotinic acid amide derivatives, adenosine derivatives, adenine derivatives, thiabenzoles, and diaminosulfones.

Examples of the nitrogenous compound having a carboxyl group include amic acid derivatives (e.g., nicotinic acid, alanine, alginine, aspargic acid, glutamic acid, glycine, hystidine, isoleucine, glycylleucine, leucine, methionine, phenylalanine, threonine, lysine, 3-aminopyradine-2-carboxylic acid, and methoxyalanine), and 2-quinoline-carboxylic acid. Examples of the nitrogenous compound having a sulfonyl group, nitrogenous compound having a hydroxyl group, nitrogenous compound having a hydroxylphenyl group, and alcoholic nitrogenous compound include 2-hydroxypyridine, aminocresole, thiaminenaphthalene disulfonate, pyridine-sulfonic acid, 2-amino-4-nitrophenol, ethanol amine, diethanol amine, triethanolamine, piperidine ethanol, 1-aminobutane-2-diol, and 1-aminopropan-3-ol.

Examples of the amide derivative include foramide, N-methylformamide, N,N-dimethylformamide, acetamide, N-methylacetamide, N,N-dimethylacetamide, propionamide, and benzamide.

The nitrogenous compound is preferably blended in an amount of about 0.001 to 4 parts, especially about 0.01 to 1 part in the resist composition of the invention. Less than 0.001 part of the nitrogenous compound would be ineffective whereas more than 4 parts of the nitrogenous compound would adversely affect resolution and sensitivity.

Examples of the surfactant include perfluoroalkyl-polyoxyethylene ethanols, fluorinated alkyl esters, perfluoroalkylamine oxides, and perfluoroalkyl EO addition products.

Examples of the light-absorbing agent include diaryl sulfoxides, diaryl sulfones, 9,10-dimethylanthracene, and 9-fluorenone.

With respect to the use of the resist composition of the invention and light exposure, any of well-known lithography techniques may be used. The resist composition of the invention is best suited for fine patterning using deep UV light of 254 to 193 nm and electron beams.

BENEFITS OF THE INVENTION

Since a novel sulfonium salt of formula (1) according to the invention possesses a substituted or unsubstituted arylsulfonate anion and has a nitrogenous aromatic group introduced therein, it generates upon light exposure a substituted or unsubstituted arylsulfonic acid which is sufficiently weaker than conventionally generated acids such as trifluoromethanesulfonic acid to minimize the influence of undesired side reaction in the post-exposure baking (PEB) step, but sufficiently stronger than alkylsulfonic acids to maintain sensitivity relatively high.

The sulfonium salt of formula (1) is effective for reducing the influence of not only deactivation of acid at the resist surface by basic compounds, but also deactivation of acid at the resist film-substrate interface, resulting in a well-defined pattern profile. When the sulfonium salt has an acid labile group, a higher dissolution contrast is expected between exposed and unexposed areas. Therefore, the sulfonium salt is useful as a component of a chemically amplified positive working resist composition having sufficiently high resolution to lend itself to fine patterning.

Where the sulfonium salt of formula (1) is used as a sole photoacid generator of a chemically amplified positive working resist composition, there is obtained a pattern profile which is little affected by basic compounds borne in air and originating from the substrate. Where the sulfonium salt of formula (1) is used in combination with an existing photoacid generator as a photoacid generator of a chemically amplified positive working resist composition, high sensitivity is ensured while maintaining a well-defined pattern profile.

The resist composition containing a novel sulfonium salt of formula (1) as a photoacid generator is highly sensitive to actinic radiation such as deep UV, electron beams and X-rays, especially KrF excimer laser beams as a chemically amplified positive resist material, can be patterned by development with alkaline aqueous solution, and has high sensitivity, resolution and resistance to plasma etching with the resulting resist pattern having improved heat resistance.

EXAMPLE

Examples of the present invention are given below by way of illustration and not by way of limitation. The synthesis of novel sulfonium salts is described prior to Examples and Comparative Examples. All parts are by weight.

Synthesis Example 1

Synthesis of tris(4-dimethylaminophenyl)sulfonium p-toluenesulfonate

A solution of 7.2 grams (0.025 mol) of bis(4-dimethylaminophenyl) sulfoxide in 110 grams of methylene chloride was cooled in an ice water bath. To the solution, 1.3 grams (0.013 mol) of triethylamine was added and 12.2 grams (0.05 mol) of trimethylsilyl-p-toluenesulfonate was added dropwise in a controlled manner so that the temperature might not exceed 10° C. The reaction solution was ripened for 30 minutes while maintaining a reaction temperature of 0° to 10° C. A Grignard reagent, which was prepared in a conventional manner using 10.0 grams (0.05 mol) of 4-bromo-N,N-dimethylaniline, 1.2 grams (0.05 mol) of magnesium and 50 grams of THF, was added dropwise to the reaction solution in a controlled manner so that the temperature might not exceed 10° C. The reaction solution was ripened for 30 minutes while maintaining a reaction temperature of 0° to 10° C. 300 grams of an aqueous solution of 20% ammonium chloride was added to the reaction solution to terminate reaction. After separation, 300 grams of chloroform was added to the organic layer. After the organic layer was washed twice with 200 grams of water, the solvent was distilled off in vacuum, yielding an oily residue. The oily residue was worked up by column chromatography (silica gel, eluent: chloroform/methanol), isolating 5.9 grams (yield 42%) of tris(4-dimethylaminophenyl) sulfonium p-toluene-sulfonate with 99% purity.

The thus obtained tris (4-dimethylaminophenyl) sulfonium p-toluenesulfonate was analyzed by nuclear magnetic resonance (NMR) spectroscopy, infrared (IR) spectroscopy, and elemental analysis. The results are shown below.

¹H-NMR (CDCl₃, δ ppm)

Structure: (CH₃)₂N—C₆H₄—S⁺(—C₆H₄—N(CH₃)₂)(—C₆H₄—N(CH₃)₂) with CH₃—C₆H₄—SO₃⁻ counterion
- labels: a = (CH₃)₂N, b,c on ring, d = CH₃ on tosylate, e,f on tosylate ring

| | | | |
|---|---|---|---|
| (a) | 3.01 | singlet | 18 H |
| (b) | 6.72–6.75 | doublet | 6 H |
| (c) | 7.23–7.26 | doublet | 6 H |
| (d) | 2.23 | singlet | 3 H |
| (e) | 6.99–7.02 | doublet | 2 H |
| (f) | 7.80–7.83 | doublet | 2 H |

IR: (cm⁻¹)

2910, 1583, 1550, 1516, 1488, 1373, 1306, 1199, 1161, 1074, 1033, 991, 943, 815, 678

Elemental analysis for $C_{31}H_{37}O_3N_3S_2$

Calcd. (%) C: 66.0 H: 6.6 N: 7.5

Found (%) C: 65.8 H: 6.8 N: 7.4

Synthesis Example 2

Synthesis of (4-tert-butoxyphenyl)bis(4-dimethylaminophenyl)-sulfonium p-toluenesulfonate A solution of 7.2 grams (0.025 mol) of bis(4-dimethylaminophenyl) sulfoxide in 200 grams of methylene chloride was cooled in an ice water bath. To the solution, 1.3 grams (0.013 mol) of triethylamine was added and 12.2 grams (0.05 mol) of trimethylsilyl-p-toluenesulfonate was added dropwise in a controlled manner so that the temperature might not exceed 10° C. The reaction solution was ripened for 30 minutes while maintaining a reaction temperature of 0° to 10° C. A Grignard reagent, which was separately prepared in a conventional manner using 11.1 grams (0.06 mol) of 4-tert-butoxychlorobenzene, 1.5 grams (0.06 mol) of magnesium and 20 grams of THF, was added dropwise to the reaction solution in a controlled manner so that the temperature might not exceed 10° C. The reaction solution was ripened for 30 minutes while maintaining a reaction temperature of 0° to 10° C. 200 grams of an aqueous solution of 20% ammonium chloride was added to the reaction solution to terminate reaction. After separation, 200 grams of chloroform was added to the organic layer. After the organic layer was washed twice with 200 grams of water, the solvent was distilled off in vacuum, yielding an oily residue. The oily residue was recrystallized, isolating 7.7 grams (yield 52%) of (4-tert-butoxyphenyl)bis(4-dimethylaminophenyl) sulfonium p-toluenesulfonate with 99% purity.

The thus obtained (4-tert-butoxyphenyl)bis(4-dimethylaminophenyl)sulfonium p-toluenesulfonate was analyzed by NMR, IR spectroscopy, ultraviolet (UV) spectroscopy, and elemental analysis. The results are shown below.

¹H-NMR (CDCl₃, δ ppm)

Structure: (CH₃)₂N—C₆H₄—S⁺(—C₆H₄—N(CH₃)₂)(—C₆H₄—OC(CH₃)₃) with CH₃—C₆H₄—SO₃⁻ counterion

| | | | |
|---|---|---|---|
| (a) | 1.38 | singlet | 9 H |
| (b) | 3.00 | singlet | 12 H |
| (c) | 6.74–6.77 | doublet | 4 H |
| (d) | 7.08–7.11 | doublet | 4 H |
| (e) | 7.36–7.42 | multiplet | 6 H |
| (f) | 2.23 | singlet | 3 H |
| (g) | 6.99–7.02 | doublet | 2 H |
| (h) | 7.80–7.83 | doublet | 2 H |

IR: (cm⁻¹)

2975, 1589, 1550, 1516, 1489, 1444, 1373, 1199, 1161, 1120, 1074, 1033, 1012, 815, 678, 568

Elemental analysis for $C_{33}H_{40}O_4N_2S_2$

Calcd. (%) C: 66.9 H: 6.8 N: 4.73

Found (%) C: 66.8 H: 6.9 N: 7.69

Synthesis Example 3

Synthesis of bis(4-tert-butoxyphenyl)(4-dimethylaminophenyl)-sulfonium p-toluenesulfonate A solution of 8.5 grams (0.025 mol) of bis(4-tert-butoxyphenyl) sulfoxide in 300 grams of methylene chloride was cooled in an ice water bath. To the solution, 1.3 grams (0.013 mol) of triethylamine was added and 12.2 grams (0.05 mol) of trimethylsilyl-p-toluenesulfonate was added dropwise in a controlled manner so that the temperature might not exceed 10° C. The reaction solution was ripened for 30 minutes while maintaining a reaction temperature of 0° to 10° C. A Grignard reagent, which was separately prepared in a conventional manner using 10.0 grams (0.05 mol) of 4-bromo-N,N-dimethylaniline, 1.2 grams (0.05 mol) of magnesium and 50 grams of THF, was added dropwise to the reaction solution in a controlled manner so that the temperature might not exceed 10° C. The reaction solution was ripened for 30 minutes while maintaining a reaction temperature of 0° to 10° C. 200 grams of an aqueous solution of 20% ammonium chloride was added to the reaction solution to terminate reaction. After separation, 200 grams of chloroform was added to the organic layer. After the organic layer was washed twice with 200 grams of water, the solvent was distilled off in vacuum, yielding an oily residue. The oily residue was recrystallized, isolating 7.6 grams (yield 49%) of bis(4-tert-butoxyphenyl)(4-dimethylaminophenyl)sul fonium p-toluenesulfonate with 99% purity.

The thus obtained bis(4-tert-butoxyphenyl)(4-dimethylaminophenyl)sulfonium p-toluenesulfonate was analyzed by NMR, IR spectroscopy, UV spectroscopy, and elemental analysis. The results are shown below.

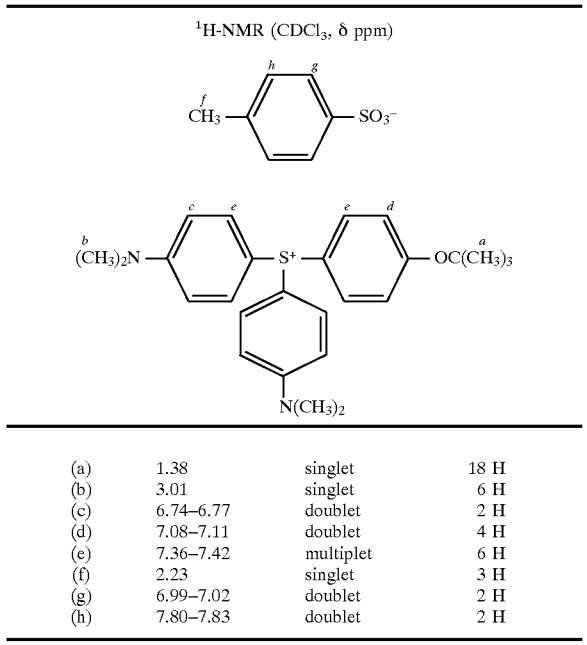

$^1$H-NMR (CDCl$_3$, δ ppm)

| | | | |
|---|---|---|---|
| (a) | 1.38 | singlet | 18 H |
| (b) | 3.01 | singlet | 6 H |
| (c) | 6.74–6.77 | doublet | 2 H |
| (d) | 7.08–7.11 | doublet | 4 H |
| (e) | 7.36–7.42 | multiplet | 6 H |
| (f) | 2.23 | singlet | 3 H |
| (g) | 6.99–7.02 | doublet | 2 H |
| (h) | 7.80–7.83 | doublet | 2 H |

IR: (cm$^{-1}$)
2976, 1589, 1550, 1516, 1489, 1444, 1373, 1199, 1161, 1121, 1074, 1032, 1012, 814, 678, 569 Elemental analysis for $C_{35}H_{43}O_5N_1S_2$ Calcd. (%) C: 67.6 H: 7.0 N: 2.25

Found (%) C: 67.2 H: 6.9 N: 2.23

Synthesis Examples 4–5

By using 4-tetrahydropyranyloxyphenyl chloride or 4-(1-ethoxyethyloxy)phenyl chloride instead of 4-tert-butoxyphenyl chloride used in Synthesis Example 2, a sulfonium salt having a 4-dimethylaminophenyl group as the nitrogenous group and a tetrahydropyranyloxyphenyl or ethoxyethyloxyphenyl group as the aromatic group having an acid labile group was obtained.

Synthesis Example 4:
bis(4-dimethylaminophenyl)(4-tetrahydropyranyloxyphenyl)sulfonium p-toluenesulfonate, yield 45%, purity 99%

Synthesis Example 5:
(4-(1-ethoxyethyloxy)phenyl)bis(4-dimethylaminophenyl)sulfonium p-toluenesulfonate, yield 42%, purity 98%

Synthesis Examples 6–7

By using bis(4-tetrahydropyranyloxyphenyl) sulfoxide or bis(4-(1-ethoxyethyloxy)phenyl) sulfoxide instead of bis(4-tert-butoxyphenyl) sulfoxide used in Synthesis Example 3, a sulfonium salt having a 4-dimethylaminophenyl group as the nitrogenous group and a tetrahydropyranyloxyphenyl or ethoxyethyloxyphenyl group as the aromatic group having an acid labile group was obtained.

Synthesis Example 6:
(4-dimethylaminophenyl)bis(4-tetrahydropyranyloxyphenyl)sulfonium p-toluenesulfonate, yield 41%, purity 99%

Synthesis Example 7:
bis(4-(1-ethoxyethyloxy)phenyl)(4-dimethylaminophenyl)sulfonium p-toluenesulfonate, yield 46%, purity 99%

Synthesis Example 8

The procedure of Synthesis Example 2 was repeated except that bis(4-(4-picolyloxy)phenyl) sulfoxide was used instead of bis(4-dimethylaminophenyl) sulfoxide in Synthesis Example 2, obtaining a sulfonium salt having a 4-(4-picolyloxy)phenyl group as the nitrogenous aromatic group and a 4-tert-butoxyphenyl group as the acid labile group. The thus obtained salt was bis(4-(4-picolyloxy)phenyl)(4-tert-butoxyphenyl)sulfonium p-toluenesulfonate in a yield of 29% and a purity of 99%.

Synthesis Example 9

The procedure of Synthesis Example 8 was repeated except that a 4-tetrahydropyranyloxyphenyl Grignard reagent was used instead of the 4-tert-butoxyphenyl Grignard reagent in Synthesis Example 8, obtaining a sulfonium salt having a 4-(4-picolyloxy)phenyl group as the nitrogenous aromatic group and a 4-tetrahydropyranyloxyphenyl group as the acid labile group. The thus obtained salt was bis(4-(4-picolyloxy)phenyl)(4-tetrahydropyranyloxyphenyl)sulfonium p-toluenesulfonate in a yield of 26% and a purity of 99%.

Synthesis Examples 10–11

The novel sulfonium salt having an acid labile group obtained in Synthesis Example 2 or 3 was deprotected using p-toluenesulfonic acid in methanol or ethanol. The resulting hydroxyphenylsulfonium salt was reacted, without isolation, with tert-butyl chloroacetate under basic condition, thereby synthesizing a sulfonium salt having a nitrogenous aromatic group and an acid labile group as shown below.

Synthesis Example 10:
bis(4-dimethylaminophenyl)(4-tert-butoxycarbonylmethyloxyphenyl)sulfonium p-toluenesulfonate, yield 20% (two steps), purity 99%

Synthesis Example 11:
(4-tert-butoxycarbonylmethyloxyphenyl)bis(4-dimethylaminophenyl)sulfonium p-toluenesulfonate, yield 26% (two steps), purity 99%

Synthesis Example 12

The tert-butoxy groups of tris(4-tert-butoxyphenyl)sulfonium p-toluenesulfonate were deprotected using p-toluenesulfonic acid in methanol. The resulting hydroxyphenylsulfonium salt was reacted with 4-(chloromethyl)pyridine under basic condition, thereby synthesizing a sulfonium salt having a 4-(4-picolyloxy)phenyl group as the nitrogenous aromatic group. The resulting sulfonium salt was tris(4-(4-picolyloxy)phenyl)sulfonium p-toluenesulfonate in a yield of 72% and a purity of 98%.

Synthesis Example 13

The novel sulfonium salt having an acid labile group obtained in Synthesis Example 2 was deprotected using p-toluenesulfonic acid in methanol or ethanol. The resulting sulfonium salt was reacted with 4-(chloromethyl)pyridine under basic condition, thereby synthesizing a sulfonium salt having a 4-dimethylaminophenyl group and a 4-(4-picolyloxy)-phenyl group as the nitrogenous aromatic group. The resulting sulfonium salt was bis(4-dimethylaminophenyl)-(4-(4-picolyloxy)phenyl)sulfonium p-toluenesulfonate in a yield of 65% and a purity of 97%.

Synthesis Examples 14–16

Sulfonium salts having a 2,4-dimethylbenzenesulfonate anion were obtained as in Synthesis Examples 1 to 3 except that trimethylsilyl-2,4-dimethylbenzenesulfonate was used instead of trimethylsilyl-p-toluenesulfonate in Synthesis Examples 1 to 3.

Synthesis Example 14:
tris(4-dimethylaminophenyl)sulfonium 2,4-dimethylbenzenesulfonate, yield 42%, purity 99%

Synthesis Example 15:
(4-tert-butoxyphenyl)bis(4-dimethylaminophenyl)sulfonium 2,4-dimethylbenzenesulfonate, yield 35%, purity 99%

Synthesis Example 16:
bis(4-tert-butoxyphenyl)(4-dimethylaminophenyl)-sulfonium 2,4-dimethylbenzenesulfonate, yield 40%, purity 99%

Examples 1–15 & Comparative Examples 1–5

Liquid resist compositions were prepared by dissolving a polyhydroxystyrene, a photoacid generator, and a dissolution inhibitor in a solvent in accordance with the formulation shown in Tables 1 and 2.

The polyhydroxystyrene was selected from a polyhydroxystyrene derivative of the following formula Polym. 1 wherein the hydrogen atom of some hydroxyl groups is protected with a tert-butoxycarbonyl group, a polyhydroxystyrene derivative of the following formula Polym. 2 wherein the hydrogen atom of some hydroxyl groups is protected with a tetrahydrofuranyl group, a polyhydroxystyrene derivative of the following formula Polym. 3 wherein the hydrogen atom of some hydroxyl groups is protected with a 1-ethoxyethyl group, and a polyhydroxystyrene derivative of the following formula Polym. 4 wherein the hydrogen atoms of some hydroxyl groups are protected with tert-butoxycarbonyl and 1-ethoxyethyl groups. The photoacid generator was selected from the onium salts of the formulae PAG. 1 to PAG. 8. The dissolution inhibitor was 2,2'-bis(4-tert-butoxycarbonyloxyphenyl)propane of the formula DRI. 1. The solvent was 1-ethoxy-2-propanol (abbreviated as EtOIPA) or a solvent mixture of ethyl lactate (85 wt %) and butyl acetate (15 wt %).

Each of the compositions was passed through a 0.2-μm Teflon® filter. It was then spin coated onto a silicon wafer to form a coating of 0.7 μm thick. With the silicon wafer rested on a hot plate at 100° C., the coating was pre-baked for 120 seconds.

The film was exposed to a pattern of light by means of an excimer laser stepper model NSR 2005EX (manufactured by Nikon K.K., numerical aperture NA=0.5), baked at 90° C. for 90 seconds, and developed with an aqueous solution of 2.38% tetramethylammonium hydroxide, obtaining a positive pattern.

The resulting resist patterns were evaluated as follows.

First, sensitivity (Eth value) was determined. Provided that the exposure dose with which the top and bottom of a 0.30-μm line-and-space pattern were resolved at 1:1 was the optimum dose (sensitivity Eop), the minimum line width of a line-and-space pattern which was recognized separate at this dose was the resolution of a test resist. The profile of the resist pattern resolved was observed under a scanning electron microscope.

The resist was further determined for PED stability by exposing at the optimum exposure dose, leaving the resist film to stand for a varying time, and baking (PEB) the film. The delay time was determined at which a change in the resist pattern configuration was observed, for example, the line pattern became a T-top profile, footing occurred at the substrate interface, or resolution became impossible. The longer the delay time, the better is the PED stability. It is noted that in Examples 14 and 15, a nitrogenous compound or carboxylic acid derivative was added as an additive for imparting PED stability.

On the silicon wafer, there was found no deactivation of the generated acid at a resist film-substrate interface, that is, no degradation of a pattern profile as by footing. Similar evaluation was done on a silicon nitride wafer. The results associated with the silicon nitride wafer are shown in Tables 1 and 2.

The results are shown in Tables 1 and 2.

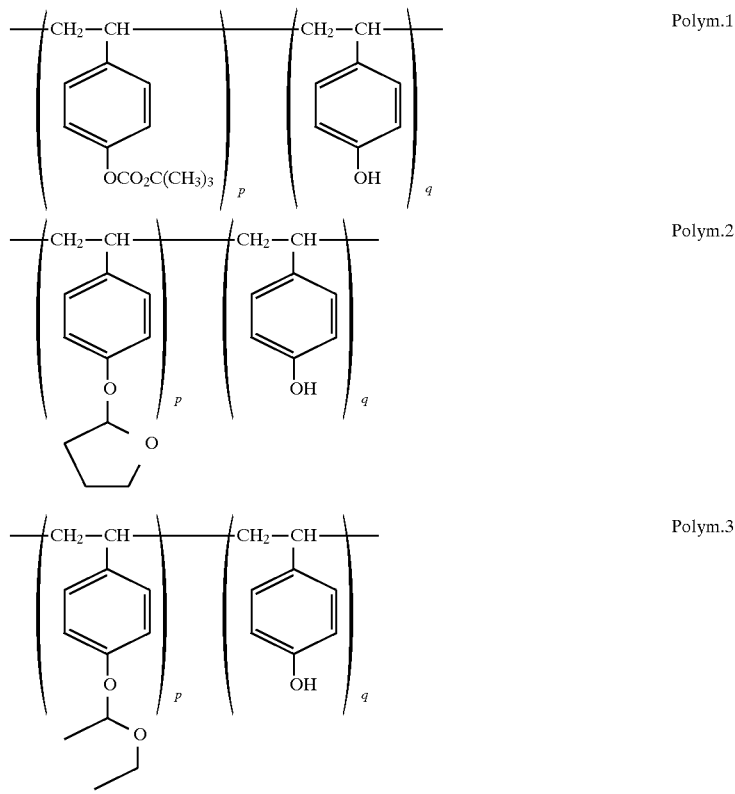

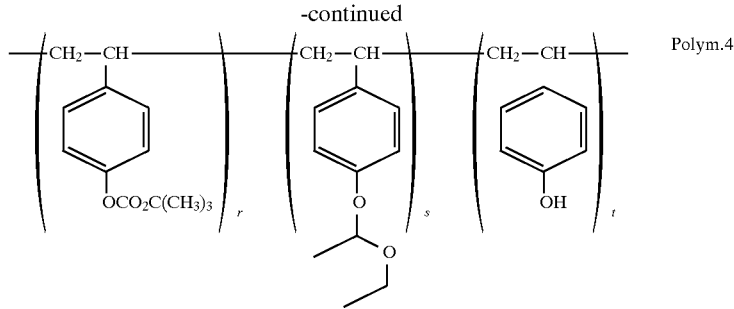
Polym.4
p/(p+q) = 0.1–0.4
(r+s)/(r+s+t) = 0.1–0.4
weight average molecular weight:
3,000–100,000
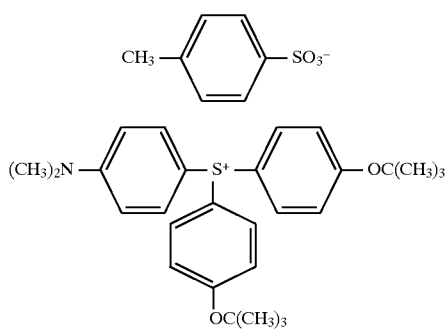
PAG.1
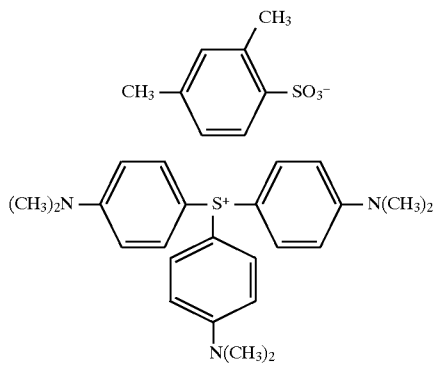
PAG.2
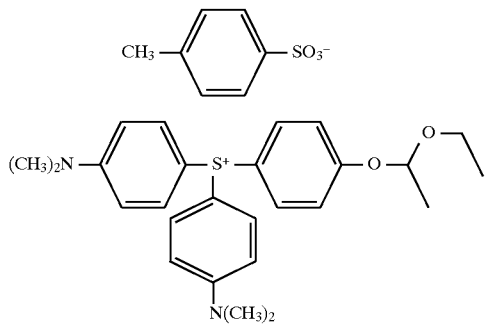
PAG.3

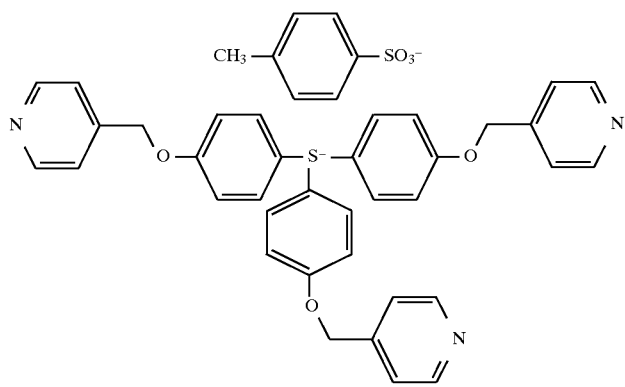
PAG.4
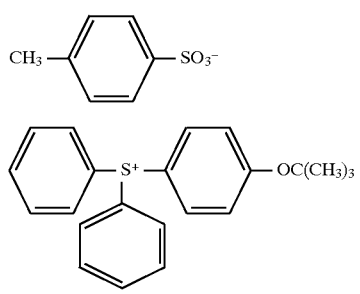
PAG.5
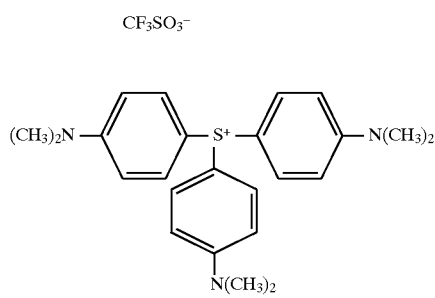
PAG.6
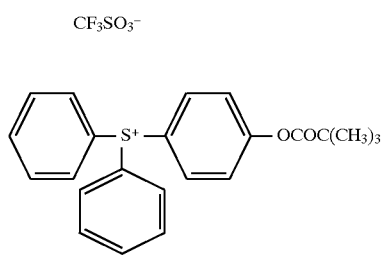
PAG.7
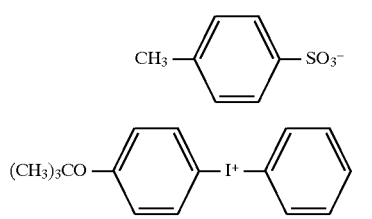
PAG.8
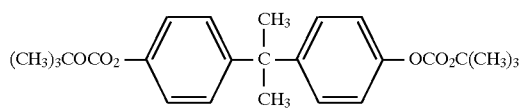
DRI.1

TABLE 1

| Example | Resist composition (pbw) Alkali soluble resin | Photoacid generator | Dissolution inhibitor | Additive | Solvent | Sensitivity Eop (mJ/cm$^2$) | Resolution ($\mu$m) | Pattern profile & footing | PED stability (min.) |
|---|---|---|---|---|---|---|---|---|---|
| E1 | Polym. 2 (40) Polym. 3 (40) | PAG. 1 (4) | DRI. 1 (20) | — | EtOIPA (500) | 35.0 | 0.28 | rectangular ± | 120 |
| E2 | Polym. 3 (80) | PAG. 2 (4) | DRI. 1 (20) | — | EtOIPA (500) | 45.0 | 0.30 | rectangular ± | 150 |
| E3 | Polym. 4 (80) | PAG. 3 (4) | DRI. 1 (20) | — | EtOIPA (500) | 40.0 | 0.28 | rectangular ± | 120 |
| E4 | Polym. 1 (80) | PAG. 1 (1) PAG. 3 (3) | DRI. 1 (20) | — | EtOIPA (500) | 30.0 | 0.26 | rectangular ± | 40 |
| E5 | Polym. 3 (80) | PAG. 2 (0.3) PAG. 5 (3.7) | DRI. 1 (20) | — | EtOIPA (450) | 16.0 | 0.24 | rectangular ± | 90 |
| E6 | Polym. 1 (37) Polym. 2 (37) | PAG. 4 (0.3) PAG. 5 (3.7) | — | — | EtOIPA (450) | 18.0 | 0.28 | rectangular ± | 60 |
| E7 | Polym. 1 (37) Polym. 3 (37) | PAG. 1 (1) PAG. 8 (3) | — | — | EtOIPA (500) | 14.0 | 0.26 | rectangular ± | 60 |
| E8 | Polym. 4 (80) | PAG. 1 (1) PAG. 7 (3) | DRI. 1 (20) | — | EtOIPA (500) | 14.0 | 0.26 | rectangular ± | 60 |
| E9 | Polym. 1 (40) Polym. 3 (40) | PAG. 3 (0.6) PAG. 8 (3.4) | DRI. 1 (10) | — | EtOIPA (500) | 16.0 | 0.26 | rectangular ± | 60 |
| E10 | Polym. 4 (80) | PAG. 1 (1) PAG. 8 (3) | DRI. 1 (20) | — | PGMEA (450) | 18.0 | 0.26 | rectangular ± | 60 |
| E11 | Polym. 4 (80) | PAG. 3 (0.6) PAG. 5 (3.4) | DRI. 1 (20) | — | EL/BA (500) | 20.0 | 0.24 | rectangular ± | 60 |
| E12 | Polym. 1 (40) Polym. 2 (40) | PAG. 2 (0.3) PAG. 8 (3.7) | DRI. 1 (20) | — | EtOIPA (500) | 22.0 | 0.26 | rectangular ± | 60 |
| E13 | Polym. 1 (40) Polym. 3 (40) | PAG. 1 (1) PAG. 5 (3) | DRI. 1 (20) | — | EtOIPA (500) | 16.0 | 0.24 | rectangular ± | 60 |
| E14 | Polym. 4 (80) | PAG. 3 (0.6) PAG. 7 (3.4) | DRI. 1 (20) | NMP (0.1) | EtOIPA (450) | 22.0 | 0.26 | rectangular ± | 90 |
| E15 | Polym. 4 (80) | PAG. 1 (1) PAG. 5 (3) | DRI. 1 (20) | BHVA (10) | EtOIPA (450) | 18.0 | 0.26 | rectangular ± | 80 |

TABLE 2

| Comparative Example | Resist composition (pbw) Alkali soluble resin | Photoacid generator | Dissolution inhibitor | Additive | Solvent | Sensitivity Eop (mJ/cm$^2$) | Resolution ($\mu$m) | Pattern profile & footing | PED stability (min.) |
|---|---|---|---|---|---|---|---|---|---|
| CE1 | Polym. 1 (80) | PAG. 5 (4) | DRI. 1 (20) | — | EtOIPA (500) | 20.0 | 0.28 | forward taper | 10 |

TABLE 2-continued

| Comparative Example | Resist composition (pbw) | | | | | Sensitivity Eop (mJ/cm$^2$) | Resolution ($\mu$m) | Pattern profile & footing | PED stability (min.) |
|---|---|---|---|---|---|---|---|---|---|
| | Alkali soluble resin | Photoacid generator | Dissolution inhibitor | Additive | Solvent | | | | |
| CE2 | Polym. 1 (40) Polym. 1 (40) | PAG. 6 (4) | DRI. 1 (20) | — | EtOIPA (500) | 200.0 | 0.30 | +++ forward taper ++ | 30 |
| CE3 | Polym. 3 (80) | PAG. 6 (1) PAG. 7 (3) | DRI. 1 (20) | — | EtOIPA (500) | 10.0 | 0.28 | forward taper ++ | 20 |
| CE4 | Polym. 1 (80) | PAG. 8 (4) | — | — | EtOIPA (500) | 14.0 | 0.32 | forward taper +++ | 10 |
| CE5 | Polym. 4 (80) | PAG. 6 (1) PAG. 7 (3) | — | — | EtOIPA (500) | 12.0 | 0.32 | forward taper ++ | 20 |

EtOIPA: 1-ethoxy-2-propanol
PGMEA: propylene glycol monomethyl ether acetate
EL/BA: a solvent mixture of ethyl lactate (85 wt %) and butyl acetate (15 wt %)
NMP: N-methylpyrrolidone
BHVA: 4,4'-bis(4-hydroxybenyl)valeric acid
Degree of footing:
+++: outstanding footing
++: footing
+: some footing
±: no footing As seen from the results of Tables 1 and 2, chemically amplified positive resist compositions within the scope of the invention have high sensitivity, high resolution, a wide range of focal depth, and environmental stability. Pattern profile degradation and a footing phenomenon are barely observed even when nitride film substrates are used.

Japanese Patent Application No. 75342/1996 is incorporated herein by reference.

Although some preferred embodiments have been described, many modifications and variations may be made thereto in the light of the above teachings. It is therefore to be understood that within the scope of the appended claims, the invention may be practiced otherwise than as specifically described.

We claim:

1. A sulfonium salt having a substituted or unsubstituted arylsulfonate anion of the following general formula (1):

$$R^1\!-\!S^+\!-\!R^3 \quad \underset{(Z)_n}{\underset{|}{\overset{R^2}{|}}}\!\!\!\!\!\bigcirc\!\!\!-\!SO_3^- \quad (1)$$

wherein each of $R^1$, $R^2$, and $R^3$ is a substituted or unsubstituted aromatic group, at least one of $R^1$, $R^2$, and $R^3$ is a substituted aromatic group having an acid labile group and at least one of the remaining two is a nitrogenous aromatic group or all of $R^1$, $R^2$, and $R^3$ are nitrogenous aromatic groups, Z is a hydrogen atom, alkyl group or alkoxy group, and letter n is an integer of 1 to 5.

2. The sulfonium salt of claim 1 wherein the aromatic group having an acid labile group is selected from the class consisting of a tert-butoxyphenyl group, tert-butoxycarbonyl-methyloxyphenyl group, (1-ethoxyethoxy) phenyl group, tetrahydropyranyloxyphenyl group, and tetrahydrofuranyloxy-phenyl group, and the nitrogenous aromatic group is selected from the class consisting of a dialkylaminophenyl group having an alkyl group with 1 to 8 carbon atoms, picolyloxyphenyl group, and pyridinyl group.

3. A chemically amplified positive resist composition comprising a sulfonium salt as set forth in claim 1.

4. A chemically amplified positive resist composition comprising
(A) an organic solvent,
(B) an alkali soluble resin,
(C) a dissolution inhibitor having an acid labile group,
(D) a sulfonium salt as set forth in claim 1, and
(E) a photoacid generator.

5. A chemically amplified positive resist composition comprising
(A) an organic solvent,
(B) an alkali soluble resin,
(D) a sulfonium salt as set forth in claim 1, and
(E) a photoacid generator.

6. The composition of claim 4 wherein said alkali soluble resin (B) is a polyhydroxystyrene in which hydrogen atoms of some hydroxyl groups are replaced by acid labile groups and which has a weight average molecular weight of about 3,000 to about 100,000.

7. The composition of claim 5 wherein said alkali soluble resin (B) is a polyhydroxystyrene in which hydrogen atoms of some hydroxyl groups are replaced by acid labile groups and which has a weight average molecular weight of about 3,000 to about 100,000.

8. The sulfonium salt of claim 1, wherein at least one of $R^1$, $R^2$ and $R^3$ is a substituted aromatic group having an acid labile group.

9. A chemically amplified positive photoresist composition comprising a sulfonium salt of claim 8.

10. The sulfonium salt of claim 1, wherein all of $R^1$, $R^2$ and $R^3$ are nitrogeneous aromatic groups.

11. A chemically amplified positive photoresist composition comprising a sulfonium salt of claim 10.

12. The sulfonium salt of claim 8, wherein the acid labile group is a tertiary alkoxy, carbonate, tertiary carboxylate, trialkylsilyloxy, acetal or ketal group.

13. The sulfonium salt of claim 10, wherein each nitrogeneous aromatic group is a dialkylaminophenyl group wherein the alkyl groups are of 1–8 carbon atoms, a picolyloxyphenyl group or a pyridinyl group.

14. The sulfonium salt of claim 1, wherein each Z is independently an alkyl group of 1–12 carbon atoms, an alkoxy group of 1–8 carbon atoms or hydrogen.

15. The sulfonium salt of claim 8, wherein the at least one nitrogeneous aromatic group is a dialkylaminophenyl group wherein the alkyl groups are of 1–8 carbon atoms, a picolyloxyphenyl group or a pyridinyl group.

16. A chemically amplified positive resist composition comprising:

(A) an organic solvent, (B) an alkali soluble resin, (C) a dissolution inhibitor having an acid labile group, (D) a sulfonium salt of formula (1) of claim 1, and (F) an onium salt of the formula (9)

$$(R^5)_a MY \qquad (9)$$

wherein $R^5$ are independently substituted or unsubstituted aromatic or aliphatic groups, M is a sulfonium or iodonium group, Y is a substituted or unsubstituted alkylsulfonate or arylsulfonate group and a is 2 or 3.

17. A chemically amplified positive resist composition comprising:

(A) an organic solvent, (B) an alkali soluble resin, (C) a dissolution inhibitor having an acid labile group, and (D) a sulfonium salt of formula (1) of claim 1.

18. A chemically amplified positive resist composition comprising:

(A) an organic solvent, (B) an alkali soluble resin, (D) a sulfonium salt of formula (1) of claim 1, and (F) an onium salt of the formula (9)

$$(R^5)_a MY \qquad (9)$$

wherein $R^5$ are independently substituted or unsubstituted aromatic or aliphatic groups, M is a sulfonium or iodonium group, Y is a substituted or unsubstituted alkylsulfonate or arylsulfonate group and a is 2 or 3.

19. A chemically amplified positive resist composition comprising:

(A) an organic solvent, (B) an alkali soluble resin, and (D) a sulfonium salt of formula (1) of claim 1.

* * * * *